US012740760B1

(12) United States Patent
Chunduru et al.

(10) Patent No.: US 12,740,760 B1
(45) Date of Patent: Sep. 22, 2026

(54) APPARATUS AND METHOD FOR RECONSTRUCTION OF ANATOMICAL STRUCTURE USING TRANSESOPHAGEAL ECHOCARDIOGRAPHY (TEE) IMAGING

(71) Applicant: Anumana, Inc., Cambridge, MA (US)

(72) Inventors: Abhijith Chunduru, Bengaluru (IN); Animesh Agarwal, San Mateo, CA (US); Suthirth Vaidya Subramany, Bengaluru (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/253,240

(22) Filed: Jun. 27, 2025

(51) Int. Cl.

| | |
|---|---|
| ***A61B 8/14*** | (2006.01) |
| ***G06T 7/11*** | (2017.01) |
| ***G06T 17/00*** | (2006.01) |
| ***G06V 10/46*** | (2022.01) |
| ***G16H 30/40*** | (2018.01) |

(52) U.S. Cl.
CPC ................ *A61B 8/145* (2013.01); *G06T 7/11* (2017.01); *G06T 17/00* (2013.01); *G06V 10/476* (2022.01); *G16H 30/40* (2018.01); *G06T 2207/10136* (2013.01); *G06T 2207/30048* (2013.01)

(58) Field of Classification Search
None
See application file for complete search history.

(56) References Cited

U.S. PATENT DOCUMENTS 12,154,273 B1 11/2024 Upadhyay et al.
12,217,361 B1 2/2025 Chunduru et al.
2018/0330538 A1* 11/2018 Petkov .................... G06T 15/06
2019/0090951 A1* 3/2019 Camus .................. A61B 8/483
2021/0137634 A1* 5/2021 Lang ...................... A61B 90/00
2023/0026942 A1* 1/2023 Meral .................... A61B 8/465
2023/0127935 A1* 4/2023 Chen .................... A61B 8/5238 382/131
2024/0000433 A1 1/2024 Karvandi et al.
2024/0293071 A1 9/2024 Constantine
2024/0366182 A1* 11/2024 Bonnefous ............. A61B 8/466
2025/0087339 A1* 3/2025 Ratcliffe .................. G06T 7/20
2025/0182883 A1* 6/2025 Argento ................ G16H 50/50

FOREIGN PATENT DOCUMENTS

CN 117582251 A 2/2024
WO 2023147544 A2 8/2023

* cited by examiner

*Primary Examiner* — Leon Viet Q Nguyen
(74) *Attorney, Agent, or Firm* — CALDWELL LLC

(57) ABSTRACT

An apparatus and method for reconstruction of anatomical structure using Transesophageal Echocardiography (TEE) imaging. The apparatus includes at least a processor and a memory communicatively connected to the at least a processor configured to receive first image data corresponding to a first sweep of the at least a transducer from the TEE probe, generate, using a 3D reconstruction model, at least a 3D model representative of the at least a structure, as a function of image data, receive second image data corresponding to a second sweep of the at least a transducer from the TEE probe, refine, using the 3D reconstruction model, the at least a 3D model as a function of the second image data, identify, using the at least a processor, a confidence score of a refined 3D model, and display, using a graphical user interface of a downstream device, the refined 3D model and the confidence score.

18 Claims, 12 Drawing Sheets

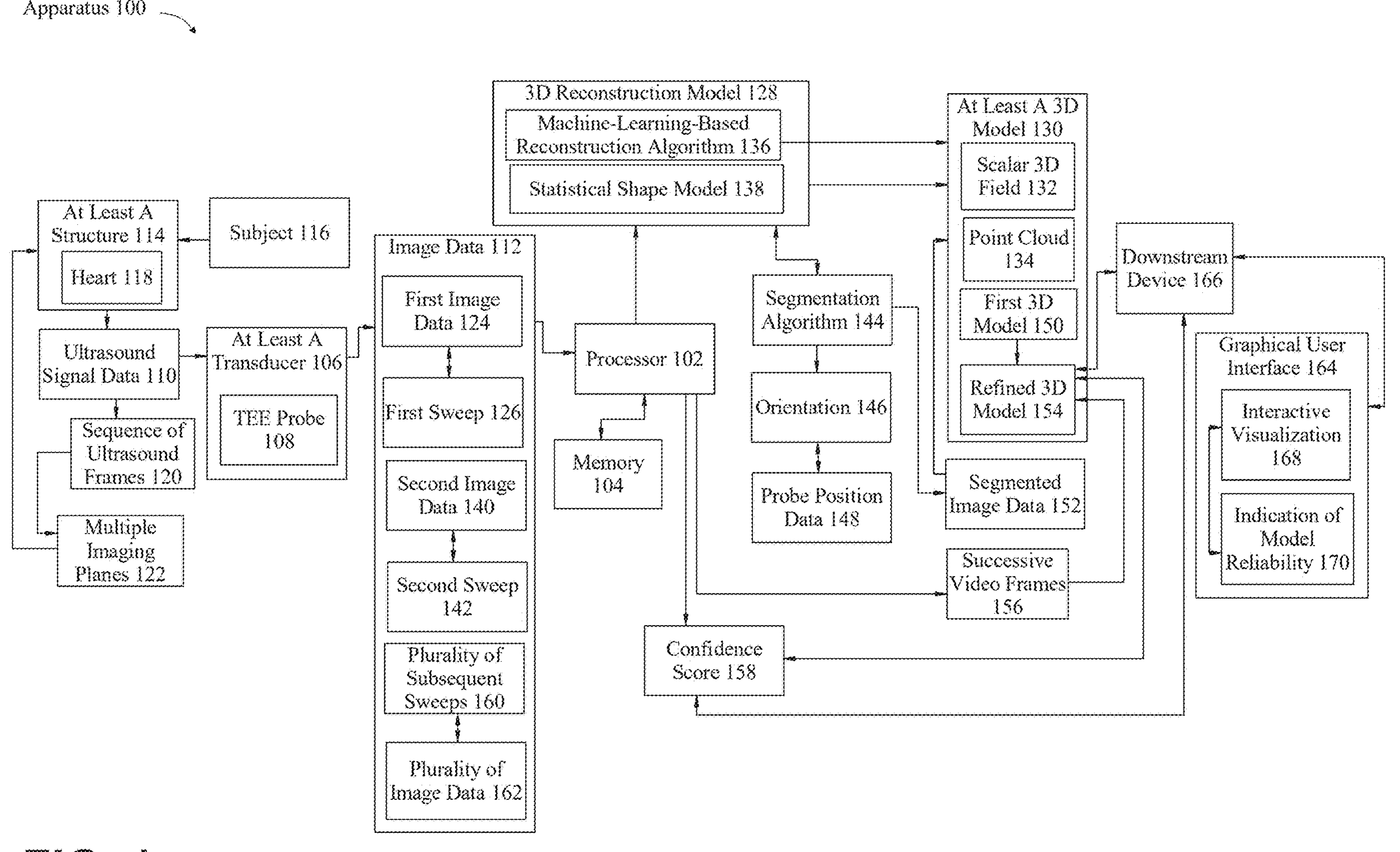
Apparatus 100
At Least A Structure 114
Heart 118
Subject 116
Ultrasound Signal Data 110
At Least A Transducer 106
TEE Probe 108
Sequence of Ultrasound Frames 120
Multiple Imaging Planes 122
Image Data 112
First Image Data 124
First Sweep 126
Second Image Data 140
Second Sweep 142
Plurality of Subsequent Sweeps 160
Plurality of Image Data 162
Processor 102
Memory 104
3D Reconstruction Model 128
Machine-Learning-Based Reconstruction Algorithm 136
Statistical Shape Model 138
Segmentation Algorithm 144
Orientation 146
Probe Position Data 148
Confidence Score 158
At Least A 3D Model 130
Scalar 3D Field 132
Point Cloud 134
First 3D Model 150
Refined 3D Model 154
Segmented Image Data 152
Successive Video Frames 156
Downstream Device 166
Graphical User Interface 164
Interactive Visualization 168
Indication of Model Reliability 170
FIG. 1

APPARATUS AND METHOD FOR RECONSTRUCTION OF ANATOMICAL STRUCTURE USING TRANSESOPHAGEAL ECHOCARDIOGRAPHY (TEE) IMAGING

FIELD OF THE INVENTION

The present invention generally relates to the field of medical image processing. In particular, the present invention is directed to an apparatus and a method for reconstruction of anatomical structure using Transesophageal Echocardiography (TEE) imaging.

BACKGROUND

TEE imaging is widely used in medical practice for detecting blood clots, assessing heart structure and function, guiding implant placement, and monitoring treatment success. However, it is predominantly 2D in nature which makes it challenging to accurately visualize and interpret complex anatomical structures. This limitation can lead to diagnostic errors and affect treatment guidance in interventional procedures.

SUMMARY OF THE DISCLOSURE

In an aspect, an apparatus for reconstruction of anatomical structure using Transesophageal Echocardiography (TEE) imaging includes at least a processor and a memory communicatively connected to the at least a processor. The memory contains instructions configuring the processor to receive first image data corresponding to a first sweep of the at least a transducer from the TEE probe, generate, using a 3D reconstruction model, at least a 3D model representative of the at least a structure, as a function of image data, receive second image data corresponding to a second sweep of the at least a transducer from the TEE probe, refine, using the 3D reconstruction model, the at least a 3D model as a function of the second image data, identify, using the at least a processor, a confidence score of a refined 3D model, and display, using a graphical user interface of a downstream device, the refined 3D model and the confidence score.

In another aspect, a method for reconstruction of anatomical structure using Transesophageal Echocardiography (TEE) imaging includes capturing, using at least a transducer of a TEE probe, ultrasound signal data and generate image data of at least a structure of a subject, receiving, using at least a processor communicatively connected to the at least a transducer, first image data corresponding to a first sweep of the at least a transducer from the TEE probe, generating, using a 3D reconstruction model, at least a 3D model representative of the at least a structure, as a function of image data, receiving, using the at least a processor, second image data corresponding to a second sweep of the at least a transducer from the TEE probe, refining, using the 3D reconstruction model, the at least a 3D model as a function of the second image data, identifying, using the at least a processor, a confidence score of a refined 3D model, and displaying, using a graphical user interface of a downstream device, the refined 3D model and the confidence score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 is a block diagram of an apparatus for reconstruction of anatomical structure using Transesophageal Echocardiography (TEE) imaging;

Figure 2A:
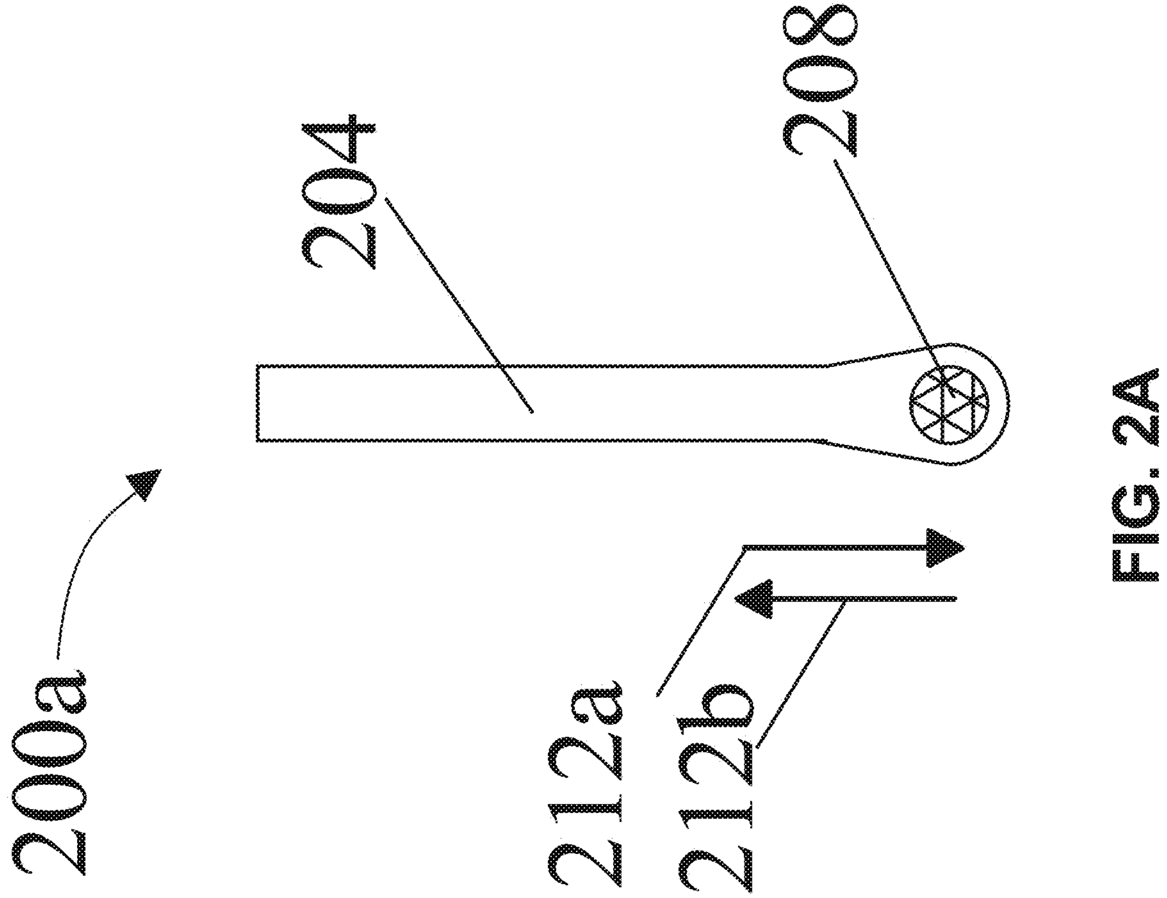
FIG. 2A is an exemplary illustration of a front view of at least a TEE probe with at least a transducer in a withdraw and an advance movement.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for reconstruction of anatomical structure using Transesophageal Echocardiography (TEE) imaging. The apparatus includes at least a computing device comprised of a processor and a memory communicatively connected to the processor. The memory instructs the processor to receive first image data corresponding to a first sweep of the at least a transducer from the TEE probe. The processor to generate, using a 3D reconstruction model, at least a 3D model representative of the at least a structure, as a function of image data. The processor to receive second image data corresponding to a second sweep of the at least a transducer from the TEE probe. Additionally, the processor refines, using the 3D reconstruction model, the at least a 3D model as a function of the second image data. The processor identifies a confidence score of a refined 3D model. The memory then instructs the processor to display, using a graphical user interface of a downstream device, the refined 3D model and the confidence score.

Referring now to FIG. 1, an exemplary embodiment of apparatus 100 for reconstruction of anatomical structure using Transesophageal Echocardiography (TEE) imaging is illustrated. Apparatus 100 may include a processor 102 communicatively connected to a memory 104. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 104 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 102 may access the information from primary memory.

Still referring to FIG. 1, apparatus 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, apparatus 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the apparatus computing device. In one or more embodiments, computing device may transmit processes to server wherein computing device may conserve power or energy.

Further referring to FIG. 1, apparatus 100 may include any "computing device" as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing devices operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting processor 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 102 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented, as a non-limiting example, using a "shared nothing" architecture.

With continued reference to FIG. 1, processor 102 may be designed and/or configured to perform any method, method step, or sequence of method steps in any embodiment described in this disclosure, in any order and with any degree of repetition. For instance, processor 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 102 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, the apparatus includes at least a TEE probe 108, the at least a TEE probe 108 includes at least a transducer 106 configured to capture ultrasound signal data 110 and generate image data 112 of at least a structure 114 of a subject 116. As used in this disclosure, a "TEE probe" is a medical device used in transesophageal echocardiography to obtain detailed ultrasound images of structures 114 within a subject 116. The TEE probe 108 may consist of a flexible endoscope with an ultrasound transducer at its tip, which may be inserted into the esophagus to provide high-resolution images of the heart 118 from a close proximity. Without limitation, this positioning may allow for enhanced visualization of cardiac anatomy and function, particularly in cases where transthoracic echocardiography may be limited by interference from the chest wall or lungs.

With continued reference to FIG. 1, for the purposes of this disclosure, a "transducer" is a device used to transform one kind of energy into another. When a transducer 106 converts a quantity of energy to an electrical voltage or an electrical current it may be called a sensor. A measurable quantity of energy may include sound pressure, optical intensity, magnetic field intensity, thermal pressure, etc. When a transducer 106 converts an electrical signal into another form of energy such as sound, light, mechanical movement, it is called an actuator. It should be noted that sound is incidentally a pressure field. Actuators allow the use of feedback at the source of the measurements.

With continued reference to FIG. 1, as used in this disclosure, "ultrasound signal data" is raw or processed information generated by an ultrasound transducer. In an embodiment, the raw or processed information may be obtained during the transmission and reception of sound waves. Without limitation, the ultrasound signal data 110 may include the reflected echoes from tissue interfaces, which are captured and converted into electrical signals for further processing. The ultrasound signal data 110 may be used to construct visual representations of anatomical structures 114, measure tissue properties, and analyze physiological functions in medical imaging applications.

With continued reference to FIG. 1, a sensor may be considered as a component or with a collection of electronics such as amplifiers, decoders, filters, computer devices and the apparatus 100. For the purposes of this disclosure an "instrument" is a sensor bundled with its associated electronics. However, in some embodiments, sensors may be further integrated with the apparatus 100.

With continued reference to FIG. 1, a sensor integrated with the apparatus 100 may be linear so that response y to a stimulus x is in the form: $y(x)=Ax$, $0 \leq x \leq x_{max}$, $A>0$. It should be noted, there is a presumption that the stimulus to be positive. A is the sensitivity of the transducer 106 gain, or the gain of the sensor. The gain is presumed to be positive for which the linear model satisfies the definition of linearity: $y(x+z)=A(x+z)=y(x)+y(z)$. It should be noted that this example is an idealized form of a sensor and may extend beyond the linearity constraints which may include time dependency, memory, and its output keeping track of input. A more generalized sensor may include the steady state transfer function of the sensor. For this case, the sensitivity can be defined as the derivative of the output with respect to the input:

$$S = \frac{\partial y}{\partial x}.$$

In this example, the sensor exhibits sensitivities to other operating parameters (i.e. supply voltage) or temperature. For the purposes of this disclosure, "sensitivity" is the ratio of output to input. This can include electrical output and signal input or an input transducer. It can also include physical output to an electrical input, or an output transducer. Sensitivity can also be used in its usual electrical meaning. In this it would refer to a percent change of a property of a device because of a percent change in a parameter. In some embodiments this would be a percent change in gain as a result of percent change in ambient temperature. This type of sensitivity may be referred to as the Gain of a sensor.

Still referring to FIG. 1, the apparatus 100 with integrated sensors may not respond to arbitrarily small signals. The apparatus 100 may respond to signals within a specified range from zero to a sensor threshold which does not cause the output of the sensor to change. The existence of a threshold relates to the nonlinear behavior of the device and the noise. The apparatus 100 with an integrated sensor may fail to respond to stimuli which are arbitrarily large as well. In this case, the apparatus 100 integrated with a sensor may have a max range. The full range of the apparatus 100 integrated with a sensor may be limited by compression or clipping. Compression and clipping are results of nonlinearity and thus may include the apparatus 100 as a nonlinearity device.

Still referring to FIG. 1, referring to the linear equation above assuming a linear sensor is improved with the addition of a constant: $y(x)=b_0+Ax$. It should be noted that the equation is not linear even though it is described as a first order polynomial. The constant is called a zero offset and can be defined in two ways: a sensor reading when the input is zero, or the value of the stimulus required to make the output zero. The zero offset is corrected by subtracting $b_0$ from y and recovering the linear description of a sensor: $y'(x)=y(x)-b_0=Ax$.

With continued reference to FIG. 1, the apparatus 100 may include very fast measurements where it can internally store energy. The apparatus 100 output may depend on previous measurements the integrated sensors make. It should be noted that the sensor may exhibit memory. The time dependence of a sensor can be linear if the response is described by a linear differential equation:

$$\sum_{n=0}^{N} A_n \frac{\partial^n y}{\partial t^n} = \sum_{k=0}^{k} B_k \frac{\partial^k x}{\partial t^k}.$$

Taking the Laplace transform of this equation:

$$y(s, X) = \left( \frac{\sum_{k=0}^{K} B_k S^k}{\sum_{n=0}^{N} A_n S^n} \right) x = H(s)X(s),$$

which is n Laplace transform space and the sensor response is still linear in stimulus x. The response of a sensor with a transfer function H(s) at time t is the convolution integral between the history of the stimulus x and the inverse Laplace transform h(t) of H(s):

$$y(t) = \int_0^\infty h(\tau)x(t-\tau)d\tau.$$

The apparatus 100 may behave like a low pass filter, wherein there is a delayed response to their input. There is a limit to the maximum stimulus frequency that can be detected. The maximum frequency a sensor can interpret is approximately the inverse of its response time.

With continued reference to FIG. 1, in an embodiment, the at least a transducer 106 may convert one form of energy into another for the purpose of sensing, measurement, or signal generation. In a non-limiting example, the at least a transducer 106 may be configured to convert electrical signals into ultrasonic waves and vice versa, enabling it to transmit and receive acoustic energy for imaging or therapeutic purposes. The transducer 106 may include piezoelectric elements, which generate ultrasonic signals when electrically stimulated, and detect returning echoes to provide data for creating detailed images of internal structures 114. In an embodiment, the transducer 106 may include an ultrasonic transducer. As used in this disclosure, an "ultrasonic transducer" is a device that converts electrical energy into ultrasonic waves and ultrasonic waves back into electrical energy for purposes such as imaging, measurement, or therapeutic applications. In a non-limiting example, an ultrasonic transducer may utilize piezoelectric elements that vibrate when an electrical signal is applied, generating high-frequency sound waves that propagate through a medium. The transducer 106 may then detect echoes of these waves reflected from structures 114 within the medium and convert them into electrical signals, which can be processed to generate images or provide diagnostic information. In an embodiment, the ultrasonic transducer may create ultrasound images by generating and detecting ultrasonic waves. As used in this disclosure, an "ultrasound image" is a visual representation generated by reflection of high-frequency sound waves off internal body structures 114. In a non-limiting example, ultrasound image may include visual representation of a heart 118 examined through esophagus. As a non-limiting example, ultrasound image may include distance between sensor and surrounding tissue or organs. In some cases, ultrasound transducer may detect ultrasound image in a plurality of angles. In a non-limiting example, ultrasound image may include a plurality of distances between sensor and a heart 118 in different angles. For example, and without limitation, when ultrasound transducer moves around within an esophagus, ultrasound transducer receives a plurality of distances between ultrasound transducer and/organ and generate ultrasound image using the plurality of distances. As another non-limiting example, ultrasound transducer may include signal strength or amplitude of ultrasonic signal emitted and received by ultrasound sensor, images within an organ, or the like. As another non-limiting example, ultrasound transducer may include ambient temperature, humidity, atmospheric pressure, or the like. In some embodiments, ultrasound transducer may be stored in a database. In some embodiments, ultrasound image may be retrieved from database. In some embodiments, user may manually input ultrasound image. In some embodiments, ultrasound image may be received from remote device. As a non-limiting example, processor 102 may receive ultrasound transducer from a computing device or processor 102 incorporated with ultrasound transducer or TEE apparatus.

With continued reference to FIG. 1, in a non-limiting example, the transducer 106 may incorporate capacitive micromachined ultrasonic transducer (CMUT) technology, which utilizes microscopic membranes to generate and receive ultrasonic waves. This configuration may allow the transducer 106 to operate at higher frequencies, enabling enhanced resolution for imaging applications such as intravascular ultrasound (IVUS) or other minimally invasive procedures. The transducer 106 may be operatively coupled to a catheter, permitting real-time imaging of internal structures 114 such as blood vessels, cardiac tissues, or other anatomical regions. As used in this disclosure, a "catheter" is a medical device designed to be inserted into a body to facilitate diagnostic, therapeutic, or interventional procedures. Catheters may include biocompatible materials such as polyurethane, silicone, or polyethylene and may include various sizes, lengths, and configurations. In a non-limiting example, a catheter may be used to introduce imaging devices, such as ultrasonic transducers, into blood vessels to capture internal anatomical information or to deliver medical treatments, such as medications or interventional tools, to targeted regions. The catheter may include features such as sensors, guide wires, or lumens to support its specific medical application. A catheter can be inserted into a coronary artery with an empty balloon and a stent attached to the end. For the purposes of this disclosure, a "stent" is a medical device designed to be implanted within a bodily lumen to restore or maintain openness by providing structural support. Stents may include tubular in shape and may include biocompatible materials such as stainless steel, cobalt-chromium alloys, nitinol (a shape-memory alloy), or biodegradable polymers. Continuing, the transducer 106 may be configured to emit and receive a plurality of ultrasonic signals to capture detailed imaging data of a structure 114, as discussed in more detail below, within the body. Without limitation, this configuration may enable real-time acquisition of three-dimensional (3D) models of anatomical structures 114, such as vascular walls or cardiac tissues, facilitating diagnostic or therapeutic procedures, as discussed more herein. In another non-limiting example, the clinician may incorporate feedback from the system, as discussed below, to dynamically adjust the position of the catheter and the transducer 106 in response to changes in the structure 114. Continuing, the transducer 106, configured to receive a plurality of ultrasonic signals, may collect data that is processed by a computing device to refine imaging outputs. For example, the apparatus may adaptively adjust the trajectory of the catheter to maintain continuous imaging of a moving target, such as a beating heart 118 or blood flow, ensuring accurate data collection and enhanced procedural outcomes.

With continued reference to FIG. 1, as used in this disclosure, "image data" is digital or analog information representing visual depictions of a structure 114, subject 116, or environment. The image data 112 may be generated through medical imaging techniques such as ultrasound, MRI, CT, X-ray, or other modalities and may include raw or processed data used for analysis, reconstruction, or diagnostic interpretation. The image data 112 may include pixel-based representations, volumetric datasets, or multi-dimensional reconstructions that facilitate visualization, measurement, and computational processing of anatomical or mechanical structures 114.

With continued reference to FIG. 1, as used in this disclosure, a "subject" is an entity that undergoes an imaging procedure. Without limitation, the subject 116 may be a patient receiving diagnostic or therapeutic intervention, or a research participant in a clinical or preclinical study. As used in this disclosure, a "structure" is a physical arrangement of components that forms an identifiable entity. Without limitation, the structure 114 may include anatomical features such as the heart 118, blood vessels, bones, muscles, soft tissues, and the like, as well as complex organ systems, connective tissues, and other physiological components that contribute to the function and integrity of a living organism. The structure 114 may encompass specialized biological formations such as cartilage, ligaments, tendons, neural networks, and the like, which play critical roles in movement, support, and signal transmission. Additionally and/or alternatively, the structure 114 may include microscopic or macroscopic elements, such as cellular matrices, extracellular scaffolding, or structural proteins that provide mechanical strength and biochemical functionality. The structure 114 may encompass medical implants, prosthetic devices, or other man-made constructs introduced into the body for therapeutic or diagnostic purposes.

With continued reference to FIG. 1, the at least a structure 114 may include a heart 118. As used in this disclosure, a "heart" is an organ responsible for pumping blood through the circulatory system. Without limitation, the heart 118 may include chambers, valves, blood vessels, and associated structures 114 that regulate the direction and efficiency of blood flow. In an embodiment, the at least a structure 114 may include a heart 118, which may be depicted as a central anatomical component within the system being analyzed or imaged. Continuing, the heart 118 may be shown in relation to surrounding structures 114, such as major blood vessels, valves, or adjacent tissues, to facilitate visualization, diagnosis, or procedural guidance. In another embodiment, the heart 118 may be assessed for structural integrity, functional performance, or pathological conditions using imaging, computational modeling, or interventional techniques.

With continued reference to FIG. 1, receiving the image data 112 of the at least a transducer 106 may include obtaining a sequence of ultrasound frames 120 corresponding to multiple imaging planes 122 of the at least a structure 114. As used in this disclosure, a "sequence of ultrasound frames" is a series of time-ordered images generated by an ultrasound system. In an embodiment, the sequence of ultrasound frames 120 may capture dynamic changes in a structure 114 over a given period. The sequence of ultrasound frames 120 may include two-dimensional (2D), three-dimensional (3D), or four-dimensional (4D) ultrasound frames, where each frame represents a snapshot of acoustic signal data processed into a visual representation. As used in this disclosure, "4D ultrasound frames" is a dynamic, time-resolved extension of three-dimensional (3D) imaging. In an embodiment, the 4D ultrasound frames may include a dynamic extension of the 3D imaging where a sequence of 3D images are captured over time to create a real-time, moving representation of a structure 114. In medical imaging, 4D ultrasound may allow for the visualization of anatomical structures 114 in motion, such as the beating of the heart 118 or the movement of lung tissues during respiration. The sequence of ultrasound frames 120 may be used for real-time imaging, motion analysis, or computational reconstruction of anatomical features to enhance diagnostic accuracy and procedural guidance.

With continued reference to FIG. 1, as used in this disclosure, "multiple imaging planes" are distinct cross-sectional views obtained from different orientations 146 during an imaging procedure. In an embodiment, the multiple imaging planes 122 may provide a more comprehensive visualization of the at least a structure 114. The multiple imaging planes 122 may be acquired using ultrasound, MRI, CT, or other imaging modalities and may include orthogonal, oblique, or custom-defined planes tailored for specific diagnostic or procedural needs. Without limitation, the multiple imaging planes 122 may capture anatomical structures 114 from various perspectives. The multiple imaging planes 122 may enhance spatial understanding, facilitate accurate measurements, and improve the detection of abnormalities or structural relationships. For example, where the structure 114 is a heart 118, the multiple imaging planes 122 may include a parasternal long-axis view, a parasternal short-axis view, an apical four-chamber view, a subcostal view, a transesophageal view, and the like, each capturing different anatomical features such as the left ventricle, right atrium, mitral valve, and aortic root. Similarly, where the structure 114 is a lung, the multiple imaging planes 122 may include anterior, lateral, and posterior lung views, allowing for the assessment of pleural effusion, pneumothorax, lung consolidation, and the like, by visualizing air-fluid interfaces and lung parenchyma from different angles. The multiple imaging planes 122 may collectively provide a more comprehensive assessment of the at least a structure 114 by leveraging the spatial and temporal information captured in the ultrasound frames of the imaging data.

Still referring to FIG. 1, processor 102 is configured to receive first image data 124 corresponding to a first sweep 126 of the at least a transducer 106 from the TEE probe 108.

As used in this disclosure, a "sweep" is a continuous movement of an imaging transducer across a region of interest to capture a series of images and/or data points. Without limitation, the sweep may be performed manually or automatically and may involve linear, rotational, or multi-directional motion to acquire comprehensive imaging information. The sweep may be used to generate the sequence of frames across multiple imaging planes 122, facilitating the reconstruction of three-dimensional (3D) or four-dimensional (4D) representations of at least a structure 114, such as the heart 118.

With continued reference to FIG. 1, in an embodiment where the structure 114 is a heart 118, the first sweep 126 may involve the controlled movement of the TEE probe 108 within the esophagus to capture a series of ultrasound frames across multiple imaging planes 122. For example, the sweep may begin with a mid-esophageal four-chamber view, where the transducer 106 is positioned to visualize all four chambers of the heart 118. As the sweep progresses, the transducer 106 may be tilted, rotated, or advanced to capture additional views, such as the mid-esophageal long-axis view, which provides a cross-sectional image of the left ventricle and aortic valve, or the transgastric short-axis view, which enables detailed assessment of left and right ventricular function. The first sweep 126 may be performed in a controlled manner to ensure that the ultrasound frames are collected sequentially and with proper alignment, allowing for the reconstruction of a three-dimensional (3D) or four-dimensional (4D) representation of the heart 118. The collected image data 112 may be processed in real time or stored for later analysis to assess structural integrity, blood flow dynamics, or the presence of pathologies such as valve dysfunction, thrombus formation, or myocardial abnormalities. The processor 102 may apply computational algorithms to enhance image quality, correct for motion artifacts, and generate composite views that integrate data from the entire sweep for improved visualization and diagnostic accuracy.

With continued reference to FIG. 1, the first sweep 126 and the second sweep 142 may include maintaining a static position and orientation of the TEE probe 108 and adjusting an orientation of the at least a transducer to acquire imaging data from different angular planes. As used in this disclosure, a "static position" is a fixed spatial placement of a component relative to its surrounding environment. In an embodiment, the static position of the TEE probe 108 may restrict or minimize translational movement along one or more axes. In an embodiment, maintaining a static position of the TEE probe may include holding the probe at a constant depth and location within the esophagus, such that image acquisition is performed without advancing, withdrawing, or laterally shifting the probe. This allows for controlled variation in imaging by adjusting the orientation or rotational angle of the transducer, while reducing variability introduced by positional changes. In an embodiment, the first sweep 126 and second sweep 130 may include rotating the transducer 106, thereby rotating the ultrasound beam, while maintaining the orientation and position of the TEE probe 108 constant. The protocol may involve restricting specific degrees of freedom (DOFs), as shown in FIGS. 2A-D, to limit TEE probe 108 translation or angulation, and instead isolate rotational motion about the transducer axis as depicted in FIG. 2E. Without limitation, by constraining the TEE probe 108 movement by the degrees of freedom as illustrated in FIGS. 2A-D, the system may ensure that changes in the imaging plane are achieved purely through beam rotation, as shown by FIG. 2E, resulting in a series of cross-sectional ultrasound frames from different angular perspectives. Continuing, this approach may enable the acquisition of consistent and anatomically registered image data, enhancing the accuracy of spatial reconstruction and downstream analysis, while minimizing motion artifacts introduced by probe manipulation.

Still referring to FIG. 1, processor 102 is configured to generate, using a 3D reconstruction model 128, at least a 3D model 130 representative of the at least a structure 114, as a function of image data 112. As used in this disclosure, a "3D reconstruction model" is a model configured to generate a three-dimensional (3D) representation of a structure 114 from acquired image data 112. The 3D reconstruction model 128 may process a sequence of ultrasound frames 120, extract spatial and depth information, and reconstruct the structure 114 in a volumetric format for enhanced visualization and analysis. The model may utilize image segmentation, interpolation, machine learning algorithms, and the like, to refine the 3D representation, enabling improved diagnostic accuracy and procedural guidance. In an embodiment, the segmentation algorithm may include edge detection techniques that analyze gradients in pixel intensity to identify the boundaries between anatomical structures or regions of interest. Without limitation, the segmentation algorithms may apply filters such as Sobel, Canny, or Laplacian operators to highlight transitions in texture, density, or brightness within the image. Continuing, by identifying areas where there is a significant change in pixel value, the segmentation algorithm may delineate sharp contours or subtle transitions, even in noisy or low-contrast images. Without limitation, this may be useful for isolating soft tissue from bone or identifying tumor margins. Once edges are defined, the system may construct bounding regions or masks around the segmented areas. Additionally and/or alternatively, a classifier may be applied to assign labels to the bounded sections, such as identifying the segmented region as a specific organ, lesion, or procedural target. In an embodiment, the classifier may be trained using supervised learning techniques on annotated medical imaging datasets, allowing it to recognize patterns and features associated with different anatomical structures or pathological findings. For example, the classifier may differentiate between liver, kidney, and spleen regions based on shape, size, texture, and spatial orientation within the scan. Without limitation, the classifier may distinguish between benign and malignant lesions by analyzing edge sharpness, internal heterogeneity, or contrast enhancement patterns. These assigned labels may be used to inform subsequent diagnostic assessments, procedural planning, or real-time image-guided interventions, enhancing the utility and precision of the overall system.

With continued reference to FIG. 1, in an embodiment where the structure 114 is a heart 118, the processor 102 may receive a sequence of ultrasound frames 120 obtained from multiple imaging planes 122 during a sweep of the TEE probe 108. Continuing, the 3D reconstruction model 128 may process this image data 112 to extract spatial, depth, and structural information, aligning and integrating the frames to create a volumetric representation of the heart 118. The reconstruction process may involve several computational steps, including image segmentation, where relevant cardiac structure 114 such as the ventricles, atria, valves, and major blood vessels are identified and isolated from the surrounding tissue. The 3D reconstruction model 128 may then perform interpolation and surface rendering, generating a smooth and continuous representation of the heart 118 by filling in gaps between imaging planes and reconstructing anatomical contours with high precision. Additionally and/or alternatively, advanced processing techniques such as motion correction and artifact reduction may be applied to enhance the clarity and accuracy of the at least a 3D model 130. Without limitation, the generated 3D model may provide a comprehensive visualization of the anatomy of the heart 118, allowing clinicians to assess structural integrity, detect abnormalities such as valve regurgitation or stenosis, plan interventional procedures with greater accuracy, and the like. In some embodiments, the 3D reconstruction model 128 may enable real-time updates, dynamically adjusting the 3D model as new ultrasound data is received, providing continuous visualization during diagnostic evaluations or surgical navigation. The 3D reconstruction model 128 may be displayed on a user interface, manipulated for different viewing angles, or integrated with additional imaging modalities for enhanced diagnostic insight as described in more detail below.

With continued reference to FIG. 1, the at least a 3D model 130 may include a scalar 3D field 132. As used in this disclosure, a "scalar 3D field" is a computational representation of a three-dimensional space where each point is assigned a scalar value that quantifies a specific property of the structure 114 being modeled. The scalar values may correspond to physical or physiological parameters such as tissue density, acoustic impedance, blood flow velocity, pressure distribution, or image intensity. The scalar 3D field 132 may be derived from image data 112 and used for visualization, analysis, or computational modeling of anatomical structures 114. In an embodiment, the at least a 3D model 130 may include a scalar 3D field 132, where each point within the reconstructed three-dimensional space is associated with a scalar value representing a characteristic of the structure 114. In an embodiment where the structure 114 is a heart 118, the scalar 3D field 132 may encode information such as tissue echogenicity (ultrasound signal intensity), allowing for differentiation between myocardium, blood-filled chambers, and valvular structures 114. The scalar values may also represent blood flow velocity, enabling visualization of hemodynamic patterns and aiding in the identification of turbulence, regurgitation, or stenosis within the cardiac cycle. Without limitation, the scalar 3D field 132 may be generated as part of the 3D reconstruction model 128, where the processor 102 assigns scalar values to each voxel in the volumetric dataset based on ultrasound signal data 110. The field may be visualized using color mapping or intensity gradients, highlighting regions of interest for diagnostic assessment. For instance, in Doppler-based ultrasound imaging, the scalar values may correspond to velocity magnitudes, assisting in evaluating blood flow dynamics and cardiac function. In another non-limiting example, where the structure 114 is a lung, the scalar 3D field 132 may represent tissue density or aeration levels, distinguishing between normal lung parenchyma, fluid accumulation, or areas of consolidation. Continuing, this may allow for enhanced diagnostic capabilities in detecting conditions such as pneumonia, pulmonary edema, or fibrosis.

With continued reference to FIG. 1, the at least a 3D model 130 may include a point cloud 134. As used in this disclosure, a "point cloud" is a collection of discrete data points in a three-dimensional coordinate system, where each point represents a specific location on the surface of a structure 114. Without limitation, the points of the point cloud 134 may be generated from imaging data, such as ultrasound frames, and may contain additional attributes such as intensity, depth, or other scalar values. In an embodiment, the point cloud 134 may be used to create a 3D representation of an anatomical structure 114 by defining its spatial geometry and surface features, which can then be processed for further visualization, segmentation, or computational modeling. In another embodiment, the at least a 3D model 130 may include a point cloud 134, where the three-dimensional structure 114 is represented as a set of data points mapped within a spatial coordinate system. In an embodiment where the structure 114 is a heart 118, the point cloud 134 may be generated by processing ultrasound image data 112 obtained from multiple imaging planes 122, capturing key anatomical landmarks such as the left and right ventricles, atria, and major blood vessels. Each point in the cloud may correspond to a detected feature within the ultrasound data, such as an edge of a cardiac chamber, a valve boundary, or a region of interest with varying echogenicity. Continuing, the point cloud 134 may serve as a foundational dataset for further 3D reconstruction, where computational algorithms interpolate and connect the points to form a continuous surface or volumetric model. In some embodiments, the point cloud 134 may be enhanced with scalar attributes, where each point carries additional information such as tissue density, Doppler velocity, or pressure measurements, facilitating advanced functional analysis of cardiac performance. Similarly, if the structure 114 is a lung, the point cloud 134 may represent the air-tissue interfaces, capturing the distribution of lung aeration and potential abnormalities such as pleural effusion or lung consolidation. The distribution of points in the cloud may help in identifying structural deformations, airflow obstructions, or other pathological conditions that impact respiratory function.

With continued reference to FIG. 1, generating the at least a 3D model 130 representative of the at least a structure 114 may include processing the image data 112 using a machine-learning-based reconstruction algorithm 136 to reconstruct volumetric representations of the at least a structure 114. As used in this disclosure, a "machine-learning-based reconstruction algorithm" is a computational model trained to generate or enhance three-dimensional (3D) representations of a structure 114 by analyzing input image data 112 and predicting volumetric spatial relationships. The machine-learning-based reconstruction algorithm 136 may leverage techniques such as deep learning, neural networks, or statistical pattern recognition to improve image quality, fill in missing data, reduce artifacts, and enhance anatomical accuracy. The machine-learning-based reconstruction algorithm 136 may be trained on large datasets of medical images to learn structural patterns and refine reconstructions dynamically, adapting to variations in image acquisition conditions and subject-specific anatomical differences. In an embodiment, generating the at least a 3D model 130 representative of the at least a structure 114 may include processing the image data 112 using the machine-learning-based reconstruction algorithm 136 to reconstruct volumetric representations of the structure 114. In an embodiment where the structure 114 is a heart 118, the machine-learning-based reconstruction algorithm 136 may analyze a sequence of ultrasound frames 120 obtained from different imaging planes and predict the missing spatial information necessary to form a complete 3D model. The machine-learning-based reconstruction algorithm 136 may use deep neural networks trained on large datasets of echocardiographic images to accurately estimate cardiac contours, enhance image resolution, and reduce noise or motion artifacts. The reconstruction process may involve multiple steps, including feature extraction, interpolation, volumetric rendering, dynamic adjustment, and the like. Without limitation, feature extraction may include identifying key anatomical landmarks such as ventricles, atria, and valves. Without limitation, interpolation and data completion may include filling in missing or occluded areas using learned patterns from similar datasets. Without limitation, volumetric rendering may include assembling the processed data into a high-fidelity 3D model with smooth and continuous surface representation. Without limitation, dynamic adjustment may include refining the model in real-time based on additional incoming ultrasound frames or user inputs. Similarly, where the structure 114 is a lung, the machine-learning-based reconstruction algorithm 136 may process ultrasound images to create a volumetric model of the lung's air-filled and solid structures 114. The machine-learning-based reconstruction algorithm 136 may enhance the differentiation between aerated and consolidated lung regions, aiding in the diagnosis of conditions such as pneumonia, pleural effusion, or pulmonary edema.

With continued reference to FIG. 1, the 3D reconstruction model 128 may include a statistical shape model 138. As used in this disclosure, a "statistical shape model" is a computational model that represents the variability of a three-dimensional (3D) structure 114 based on statistical analysis of a dataset of similar shapes. The statistical shape model 138 may be constructed by analyzing a large number of examples of the structure 114 to determine common patterns, variations, and principal modes of deformation. The statistical shape model 138 may be used to reconstruct, refine, or predict anatomical structures 114 by fitting new image data 112 to learned shape constraints, thereby improving accuracy and consistency in 3D modeling. In an embodiment, the 3D reconstruction model 128 may include the statistical shape model 138, which may enable the generation of a 3D representation of a structure 114 by utilizing statistical patterns derived from previously collected anatomical data. In an embodiment where the structure 114 is a heart 118, the statistical shape model 138 may be built from a dataset of 3D heart 118 scans obtained from multiple subjects, capturing common variations in size, shape, and anatomical landmarks. When applied to new ultrasound image data 112, the statistical shape model 138 may adapt the reconstructed heart 118 shape to align with typical structural characteristics, ensuring a more anatomically accurate and complete representation, even in cases where image data 112 is missing or noisy. The statistical shape model 138 may define a mean shape based on a training dataset and identify modes of variation that reflect natural differences among individuals. The statistical shape model 138 may further refine the 3D reconstruction by fitting it to the subject-specific image data 112 while maintaining realistic anatomical constraints, thereby enhancing spatial consistency and reducing artifacts.

With continued reference to FIG. 1, in a non-limiting example, 3D reconstruction model may be consistent with one or more aspects of the machine learning model used to generate a three-dimensional (3D) model of cardiac anatomy described in U.S. patent application Ser. No. 18/376,688, filed on Oct. 4, 2023, titled "APPARATUS AND METHODS FOR GENERATING A THREE-DIMENSIONAL (3D) MODEL OF CARDIAC ANATOMY VIA MACHINE-LEARNING," which is incorporated by reference herein in its entirety.

With continued reference to FIG. 1, in a non-limiting example, 3D reconstruction model may be consistent with one or more aspects of the heart model described in U.S. patent application Ser. No. 18/389,513, filed on Nov. 14, 2023, titled "APPARATUS AND METHODS FOR SYNTHETIZING MEDICAL IMAGES," which is incorporated by reference herein in its entirety.

With continued reference to FIG. 1, in a non-limiting example, 3D reconstruction model may be consistent with one or more aspects of the apparatus for generating a three-dimensional (3D) model of cardiac anatomy via machine-learning described in U.S. patent application Ser. No. 18/426,604, filed on Jan. 30, 2024, titled "APPARATUS AND METHOD FOR GENERATING A THREE-DIMENSIONAL (3D) MODEL OF CARDIAC ANATOMY BASED ON MODEL UNCERTAINTY," which is incorporated by reference herein in its entirety.

Still referring to FIG. 1, processor 102 is configured to receive second image data 140 corresponding to a second sweep 142 of the at least a transducer 106 from the TEE probe 108. In an embodiment where the structure 114 is a heart 118, the second sweep 142 may involve repositioning or adjusting the TEE probe 108 to capture additional ultrasound frames from different imaging planes, enhancing the comprehensiveness of the 3D reconstruction. This second sweep 142 may be performed to refine the anatomical visualization, improve spatial resolution, or provide updated data for real-time assessment of cardiac structures 114. The second sweep 142 may focus on capturing complementary views that were not fully visualized during the first sweep 126. For example, if the first sweep 126 primarily acquired mid-esophageal views, the second sweep 142 may include transgastric, deep transgastric, or high esophageal views to obtain better imaging of the left and right ventricles, heart 118 valves, or outflow tracts. Additionally, the second sweep 142 may be conducted with different ultrasound settings, such as Doppler imaging, to assess blood flow dynamics, pressure gradients, or valvular function in greater detail. The processor 102 may use the second image data 140 to update or refine the existing 3D reconstruction, correcting for motion artifacts, improving alignment, or incorporating newly captured features. In some embodiments, the second sweep 142 may serve to verify initial findings, track changes over time, or provide additional imaging perspectives to enhance diagnostic accuracy and procedural guidance. Without limitation, the integration of the second sweep 142 into the 3D reconstruction model 128 may allow the apparatus to generate a more detailed and precise volumetric representation of the heart 118, supporting improved clinical decision-making and interventional planning.

Still referring to FIG. 1, processor 102 is configured to refine, using the 3D reconstruction model 128, the at least a 3D model 130 as a function of the second image data 140. In an embodiment where the structure 114 is a heart 118, the second image data 140 may provide additional ultrasound frames obtained from a second sweep 142 of the TEE probe 108, capturing new imaging planes or improving the resolution of previously acquired data. The 3D reconstruction model 128 may process this second image data 140 to enhance the accuracy, completeness, and spatial coherence of the existing 3D model. The refinement process may include several computational adjustments to improve the 3D representation. The processor 102 may use the second image data 140 to fill in missing anatomical details, improving structural continuity and reducing gaps in the volumetric reconstruction. Additionally, the model may perform alignment corrections, ensuring that data from both sweeps are properly integrated to maintain anatomical consistency. The refinement may also involve motion compensation, where artifacts caused by cardiac movement or probe repositioning are minimized, resulting in a clearer and more stable 3D representation. In some embodiments, the second image data 140 may provide functional insights, such as updated Doppler measurements of blood flow dynamics, enabling the model to incorporate hemodynamic information into the 3D visualization. The refined 3D model 154 may be used for enhanced diagnostic evaluation, pre-procedural planning, or real-time guidance during interventional procedures.

With continued reference to FIG. 1, the apparatus may include a refinement model. The refinement model may receive a first 3D reconstruction model and new sweep data to generate the at least a 3D model 130. In an embodiment, the refinement model may further receive the first image data 124 associated with the first sweep 126 and the second image data 140 associated with the second sweep 142 to generate the at least a 3D model 130. Without limitation, by analyzing and integrating both sets of image data, the refinement model may resolve inconsistencies, reduce artifacts, add anatomical detail, and the like to generate a more complete and precise 3D model 130. Without limitation, this approach may enable more accurate diagnostic visualization and improved guidance for clinical procedures by continuously adapting the 3D model as new image information becomes available.

Still referring to FIG. 1, processor 102 is configured to identify, using the at least a processor 102, a confidence score 158 of a refined 3D model 154. As used in this disclosure, a "confidence score" is a value that quantifies the reliability of a computed result. In an embodiment, the value may be numerical or probabilistic. In an embodiment, the confidence score 158 may be associated with the reliability and/or accuracy of the generated 3D model, image segmentation, or diagnostic prediction. The confidence score 158 may be derived from various factors, including data quality, model certainty, signal strength, consistency across multiple imaging planes 122, user feedback, output from one or more machine learning models as described herein such as the 3D reconstruction model, and the like. Without limitation, a higher confidence score 158 may indicate greater accuracy and reliability of the generated output, while a lower confidence score 158 may suggest potential uncertainty or the need for additional data refinement.

With continued reference to FIG. 1, as used in this disclosure, a "refined 3D model" is a three-dimensional representation of a structure 114 that has been enhanced or updated through the incorporation of additional image data 112, computational adjustments, or corrective processing. The refinement process may involve improving spatial accuracy, reducing artifacts, increasing resolution, or integrating new imaging perspectives to provide a more complete and detailed visualization of the structure 114. A refined 3D model 154 may be generated by processing sequential image data 112, aligning multiple imaging planes 122, or applying machine-learning-based reconstruction algorithms 136 to enhance structural coherence and diagnostic reliability.

With continued reference to FIG. 1, the confidence score 158 may represent a quantitative measure of the reliability or accuracy of the reconstructed 3D representation, providing an indication of how well the model reflects the actual anatomical structure 114. In an embodiment where the structure 114 is a heart 118, the confidence score 158 may be based on factors such as the quality of ultrasound image data 112, the alignment of multiple imaging planes 122, and the completeness of volumetric reconstruction. For instance, if the TEE probe 108 captures high-resolution, artifact-free images from multiple angles, the confidence score 158 may be relatively high, indicating a well-defined and anatomically accurate 3D model. However, if the imaging data contains noise, shadowing artifacts, or gaps in coverage, the confidence score 158 may be lower, suggesting potential inaccuracies or areas that may require further refinement. Without limitation, the confidence score 158 may be influenced by motion artifacts or inconsistencies between multiple sweeps. For instance, without limitation, if the first sweep 126 and the second sweep 142 of data align well and show minimal variation, the confidence score 158 may increase, reinforcing the reliability of the reconstructed model. Conversely, if discrepancies exist between scans due to patient movement or probe repositioning, the confidence score 158 may be adjusted accordingly. The confidence score 158 may further be utilized for decision support, where a higher score may validate the model for clinical use, while a lower score may prompt additional imaging, manual review, or alternative reconstruction techniques. In some embodiments, the confidence score 158 may be visually represented within a user interface, providing real-time feedback to clinicians on the reliability of the refined 3D model 154 for diagnosis, treatment planning, or interventional guidance as described in more detail below.

With continued reference to FIG. 1, the 3D reconstruction model 128 may be configured to segment, using a segmentation algorithm 144, the at least a structure 114 in each frame of the image data 112, determine, using the 3D reconstruction model 128, an orientation 146 of the at least a transducer 106 based on probe position data 148 obtained from the transducer 106 comprising the TEE probe 108, construct, using the 3D reconstruction model 128, a first 3D model 150 of the at least a structure 114 as a function of segmented image data 152 and the orientation 146 of the at least a transducer 106, and iteratively refine, using the 3D reconstruction model 128, the first 3D model 150 using successive video frames 156 of the second image data 140 to generate the refined 3D model 154. As used in this disclosure, a "segmentation algorithm" is a computational method designed to partition image data 112 into distinct regions or categories based on predefined criteria. In an embodiment, the predefined criteria may include, without limitation, intensity, texture, anatomical features, and the like. The segmentation algorithm 144 may be used to identify and delineate specific structures 114 within medical imaging data, such as organs, tissues, or pathological regions, enabling more precise analysis and visualization. The segmentation algorithm 144 may leverage techniques such as thresholding, edge detection, clustering, or machine-learning-based approaches to enhance accuracy and adapt to variations in image quality and anatomical differences.

With continued reference to FIG. 1, as used in this disclosure, "orientation" is the spatial position and angular alignment of an object within a coordinate system. Without limitation, the orientation 146 may define the direction and tilt of the ultrasound beam relative to the structure 114 being imaged, influencing the quality and perspective of the acquired image data 112. As used in this disclosure, "probe position data" is information obtained from an imaging probe that describes its spatial location, angle, rotation, and movement relative to the subject 116 being scanned. Without limitation, the probe position data 148 may be derived from internal motion sensors, electromagnetic tracking, or mechanical encoding mechanisms within the probe and may be used to accurately align and reconstruct image data 112 within a three-dimensional space. As used in this disclosure, "successive video frames" are a sequential series of image frames captured over time. In an embodiment, the successive video frames 156 may form a dynamic representation of the at least a structure 114. In an embodiment, the successive video frames 156 may capture continuous movement of anatomical features, such as the beating of the heart 118, and may be used for real-time analysis, temporal tracking, or iterative refinement of a 3D model.

With continued reference to FIG. 1, in an embodiment where the structure 114 is a heart 118, the segmentation algorithm 144 may analyze each frame of ultrasound image data 112 obtained during a sweep of the TEE probe 108, identifying and delineating cardiac structures 114 such as the left ventricle, right ventricle, atria, valves, major blood vessels, and the like. Continuing, this segmentation may enhance the clarity of the 3D model by isolating relevant anatomical features from background noise and irrelevant tissue. Once segmentation is performed, the 3D reconstruction model 128 may use probe position data 148 to determine the orientation 146 of the TEE probe 108, ensuring that each ultrasound frame is spatially aligned with the correct anatomical coordinates. For example, without limitation, if the TEE probe 108 is positioned at a mid-esophageal long-axis view, the system may use the probe's angle and tilt data to correctly register the corresponding ultrasound slices within the volumetric reconstruction. After establishing segmentation and probe orientation 146, the 3D reconstruction model 128 may generate a first 3D model 150 of the heart 118, integrating segmented image data 152 from multiple imaging planes 122 to construct an initial volumetric representation. However, this initial model may require further refinement to enhance accuracy and detail. To achieve this, the 3D reconstruction model 128 may iteratively refine the first 3D model 150 using successive video frames 156 captured during a second imaging sweep. Continuing, the successive frames may provide updated structural information, reducing gaps in the 3D model, compensating for motion artifacts, and improving spatial resolution. For instance, without limitation, if the first model contains areas of uncertainty due to incomplete data capture in the initial sweep, the successive video frames 156 may fill in missing anatomical features, such as more precise valve morphology or dynamic changes in heart 118 chamber volume during systole and diastole. The refined 3D model 154 may therefore incorporate both initial and newly acquired image data 112, enhancing structural accuracy and functional visualization. This refined model may then be used for diagnostic evaluation, procedural planning, or real-time guidance in interventional cardiology applications.

With continued reference to FIG. 1, iteratively refining, using the 3D reconstruction model 128, is a function of the confidence score 158 and a plurality of subsequent sweeps 160, wherein the plurality of subsequent sweeps 160 may include a plurality of image data 162. In an embodiment, without limitation, the refinement process may involve continuously updating the 3D model by incorporating additional imaging data obtained through multiple sweeps of the TEE probe 108, with adjustments being guided by the confidence score 158, which may indicate the reliability of the current reconstruction. In an embodiment where the structure 114 is a heart 118, the confidence score 158 may serve as a metric to assess the accuracy of the initial 3D reconstruction, factoring in data consistency, image clarity, and spatial completeness. If the confidence score 158 is high, indicating that the 3D reconstruction model 128 has generated a reliable and well-defined representation of the heart 118, fewer refinements may be necessary. However, if the confidence score 158 is low, suggesting areas of uncertainty, noise, or missing anatomical details, the 3D reconstruction model 128 may prompt additional sweeps to enhance the model. The plurality of subsequent sweeps 160 may involve repositioning the TEE probe 108 to capture new ultrasound imaging planes that were not sufficiently visualized in previous sweeps. For example, if the initial sweep primarily focused on mid-esophageal views, subsequent sweeps may include transgastric, deep transgastric, or high esophageal views to obtain more detailed imaging of cardiac structures 114 such as the left ventricle, right atrium, mitral valve, and aortic root. Each additional sweep may provide a plurality of image data 162, allowing the 3D reconstruction model 128 to incorporate new frames, align them with existing data, and iteratively refine the 3D model to improve accuracy and resolution. Without limitation, by integrating multiple sweeps, the refinement process may correct for motion artifacts, enhance boundary definitions of cardiac structures 114, and provide a more comprehensive volumetric representation. In some embodiments, the confidence score 158 may dynamically adjust throughout the refinement process, increasing as more high-quality image data 112 is integrated. Continuing, the refined 3D model 154 may achieve a higher level of precision, offering improved visualization for diagnostic assessments, interventional planning, or real-time procedural guidance in applications such as valve repair, septal defect closure, or catheter-based interventions.

Still referring to FIG. 1, processor 102 is configured to display, using a graphical user interface 164 of a downstream device 166, the refined 3D model 154 and the confidence score 158. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface 164. For example, links to decentralized platforms as described in this disclosure may be incorporated using icons. Using an icon may be a fast way to open documents, run programs etc. because clicking on them yields instant access.

With continued reference to FIG. 1, in an embodiment, the graphical user interface 164 and an event handler may operate together to enable seamless interaction between the user and the apparatus 100. The GUI serves as the visual and interactive layer through which the user engages with the apparatus 100, presenting elements such as buttons, sliders, input fields, and informational displays. The event handler, on the other hand, functions as the underlying mechanism that monitors and responds to user interactions with the GUI. For example, when a user clicks a button on the GUI to request an explanation of a concept, the event handler may detect the click event, identify its context, and trigger the appropriate processes within the apparatus 100 to generate a tailored response. This interplay may ensure dynamic and responsive system behavior, as the event handler processes various input events such as clicks, taps, keystrokes, or voice commands, and relays these inputs to the relevant system components. The GUI subsequently updates to reflect the system's responses, such as displaying output, modifying visual elements, or providing real-time feedback. Together, the GUI and event handler create an intuitive and interactive experience, bridging user actions and system functionality to achieve efficient and personalized outcomes.

With continued reference to FIG. 1, an "event handler," as used in this disclosure, is a module, data structure 114, function, and/or routine that performs an action in response to an event. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to a user in response to such requirements.

With continued reference to FIG. 1, as used in this disclosure, a "visual element" is a component or feature within a system, display, or interface that conveys information through visual means. In a non-limiting example, the visual element may include text, images, icons, shapes, colors, and/or other graphical components designed to be perceived by the user. In a non-limiting example, the visual element may aid in communication, navigation, and/or interaction with the system. Without limitation, the visual element may be used to enhance user experience, guide behavior, and/or represent data visually in an intuitive or informative way. A visual element may include data transmitted to display device, client device, and/or graphical user interface 164. In some embodiments, visual element may be interacted with. For example, visual element may include an interface, such as a button or menu. In some embodiments, visual element may be interacted with using a user device such as a smartphone, tablet, smartwatch, or computer.

With continued reference to FIG. 1, in an embodiment, the apparatus 100 and/or the downstream device 166 may include a data structure 114. With continued reference to FIG. 1, as used in this disclosure, "data structure" is a way of organizing data represented in a specialized format on a computer configured such that the information can be effectively presented in a graphical user interface 164. In some cases, the data structure includes any input data. In some cases, the data structure contains data and/or rules used to visualize the graphical elements within a graphical user interface 164. In some cases, the data structure may include any data described in this disclosure. In some cases, the data structure may be configured to modify the graphical user interface 164, wherein data within the data structure may be represented visually by the graphical user interface 164. In some cases, the data structure may be continuously modified and/or updated by processor 102, wherein elements within graphical user interface 164 may be modified as a result. In some cases, processor 102 may be configured to transmit display device and/or the downstream device 166 the data structure. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio, and microwave data and/or signals, combinations thereof, and the like, among others. Processor 102 may transmit the data described above to a database wherein the data may be accessed from the database. Processor 102 may further transmit the data above to a display device, client device, or another computing device. The data structure may serve as the organizational framework that stores, retrieves, and manages data required for processing events and updating the GUI. The data structure may act as a bridge between the user's input, captured by the event handler, and the output displayed on the GUI, ensuring that information is handled efficiently and accurately throughout the interaction. For example, without limitation, when a user interacts with a dropdown menu in the GUI to select a topic, the event handler may capture this input and accesses a data structure, such as a dictionary or tree, that maps each topic to its associated resources or actions. The data structure may retrieve the relevant information such as, text explanations, videos, or interactive exercises, and passes it back to the event handler, which may then trigger the appropriate updates to the GUI, such as displaying the selected topic's content. In another embodiment, the data structure may also maintain the state of the system, tracking user progress, preferences, and session history. For instance, without limitation, a hash table may store user specific configurations, such as preferred learning styles or recent activity, which the event handler references when processing interactions. The GUI may then dynamically adapt to display content aligned with these configurations. This integration may ensure that user inputs are seamlessly translated into meaningful system outputs, with the data structure enabling rapid access, consistency, and scalability throughout the process. As used in this disclosure, a "hash table" is a data structure that stores data in a way that allows for fast retrieval, insertion, and deletion of elements. The hash table may organize data into key-value pairs, where each key is unique and used to identify its corresponding value. A hash table may use a hash function to compute an index, or hash code, from the key, which determines where the key-value pair is stored within an array or list.

With continued reference to FIG. 1, as used in this disclosure, an "interactive element" is a component or feature within a graphical user interface 164 (GUI) that allows users to perform actions, provide input, or engage with the apparatus 100. Interactive elements may be designed to facilitate two-way communication between the user and the system, enabling the user to influence the behavior of the apparatus or obtain feedback in response to their actions. Examples of interactive elements may include buttons, dropdown menus, sliders, checkboxes, input fields, and hyperlinks. More advanced interactive elements may include drag-and-drop interfaces, interactive diagrams, or dynamically updating content areas that respond to user actions in real time. The interactive elements may enhance user engagement by providing intuitive and responsive mechanisms for interacting with the system. Interactive elements may operate by responding to user actions such as clicks, taps, swipes, or keyboard inputs, and triggering predefined system behaviors or processes. The execution of the interactive elements may require a combination of front-end and back-end technologies that work together to provide seamless functionality and user interaction. On the front end, technologies such as HTML and CSS may define the structure, appearance, and layout of the interactive elements, while JavaScript may enable dynamic functionality. For example, without limitation, JavaScript may detect when the user clicks a button and trigger actions or animations. Front-end frameworks like React, Angular, or Vue.js may further enhance development by offering reusable components and efficient rendering mechanisms. On the back end, the system may process the user's input, retrieve the necessary data, and communicate with the front end to provide an appropriate response. APIs may act as a bridge between the front end and back end, facilitating data transfer, such as sending a user's form submission to the server and retrieving processed results. Server-side logic, implemented using languages like Python, Java, or Node.js, may handle input processing and return relevant data, such as a user's profile or quiz questions. Additional supporting technologies may ensure the smooth operation of interactive elements. Event listeners, for instance, may continuously monitor for specific actions like mouse clicks or text entries, executing code when such events are detected. Efficient data structures, such as hash tables or dictionaries, may store interactive state data, such as user preferences or settings, for quick access and updates. Databases, including MySQL or MongoDB, may manage and store the data required for interactive features, such as user profiles or historical activity. Communication technologies may also help maintain the responsiveness of interactive elements. AJAX (Asynchronous JavaScript and XML) may allow the front end to update portions of a web page without requiring a full page reload, enhancing responsiveness. WebSockets may provide real-time interaction capabilities, such as live chats or collaborative tools, by enabling persistent communication between the client and the server. Without limitation, the apparatus 100 may include one or more APIs. As used in this disclosure, an "application programming interface (API)" is a set of defined protocols, tools, and methods that allow different software applications, systems, or components to communicate and interact with each other. An API may act as an intermediary that enables a client application, such as a user-facing app, to send requests to a server or service and receive the necessary responses, facilitating seamless integration and functionality across diverse systems.

With continued reference to FIG. 1, displaying the at least a 3D model 130 and the confidence score 158 may include rendering an interactive visualization 168 of the at least a 3D model 130 on a graphical user interface 164 and overlaying an indication of model reliability 170 based on the confidence score 158. As used in this disclosure, an "interactive visualization" is a dynamically generated graphical representation of data. In an embodiment, the interactive visualization 168 may allow a user to manipulate, explore, or modify the at least a 3D model 130 in real time. The interactive visualization 168 may enable users to adjust viewing angles, zoom, rotate, annotate, or apply filtering techniques to enhance the interpretation of complex structures. Without limitation, the interactive visualization 168 may facilitate better understanding of anatomical features, support diagnostic assessments, and improve procedural planning by providing a user-controlled, adaptable representation of image data 112. As used in this disclosure, an "indication of model reliability" is a visual and/or numerical representation that conveys the reliability information. In an embodiment, the reliability information may include accuracy, completeness, and/or confidence level of the at least a 3D model 130. The indication of model reliability 170 may be derived from the confidence score 158, which may quantify the quality of the reconstructed model based on factors such as image clarity, data consistency, and the completeness of anatomical structures 114. The indication may be displayed using color coding, transparency levels, numerical ratings, or graphical overlays to help users assess areas of higher or lower reliability within the model.

With continued reference to FIG. 1, the interactive visualization 168 may allow users to manipulate the 3D model by rotating, zooming, adjusting viewing angles, and the like to analyze anatomical structures 114 in detail. The indication of model reliability 170 may provide real-time feedback on the accuracy of different regions of the model, helping users interpret the at least a 3D model 130 with greater confidence. In an embodiment where the structure 114 is a heart 118, the indication of model reliability 170 may be presented as a color-coded overlay where high-confidence regions, such as well-defined ventricular walls or clear valve structures 114, may be highlighted in green, while areas with lower confidence due to missing data or motion artifacts may appear in yellow or red. For example, if the TEE probe 108 encountered imaging limitations due to probe angulation or interference, the at least a 3D model 130 may show a lower confidence region in the left atrial appendage, alerting clinicians that additional imaging may be required for more accurate assessment. In another example where the structure 114 is a lung, the indication of model reliability 170 may involve opacity adjustments, where areas reconstructed with high confidence may appear solid and detailed, whereas lower-confidence regions, such as lung periphery with weak ultrasound signals, may appear semi-transparent. Continuing, this may assist clinicians in determining whether additional imaging sweeps or manual validation of the reconstruction is necessary. Without limitation, the confidence score 158 and the indication of model reliability 170 may also be displayed as a numerical value on the GUI, providing an overall measure of model accuracy. For instance, a confidence score 158 of 95% may indicate a highly reliable reconstruction, while a score below 70% may suggest potential inaccuracies. Additionally and/or alternatively, users may interact with the visualization by selecting specific regions of interest, prompting the system to display localized confidence scores 158 or suggest additional imaging actions to enhance model quality.

Referring now to FIG. 2A, an exemplary illustration 200*a* of a front view of at least a TEE probe with at least a transducer in a withdraw and an advance movement. In an embodiment, the illustration 200*a* may include at least a TEE probe 204. In an embodiment, the illustration 200*a* may include at least a transducer 208. In an embodiment, the illustration 200*a* may include a withdraw and an advance movement 212*a-b* of the at least a TEE probe 204. As used in this disclosure, an "advance movement" is the forward motion of a TEE probe. In an embodiment, the advance movement 212*a* may include the at least a TEE probe 204 inserted deeper into the esophagus or stomach to capture imaging from different anatomical perspectives. Continuing, the advance movement 212*a* may allow for visualization of deeper structures, such as the transgastric short-axis view of the heart, where the probe is positioned in the stomach to obtain high-resolution images of the ventricles and outflow tracts. As used in this disclosure, a "withdraw movement" is the backward motion of a TEE probe 204. In an embodiment, the withdraw movement 212*b* may include the at least a TEE probe 204 being retracted toward the upper esophagus to obtain imaging from a different set of views. The withdraw movement 212*b* may enable imaging from higher esophageal positions, such as the mid-esophageal four-chamber view, which provides a comprehensive look at the atria, ventricles, and valve structures.

Figure 2B:
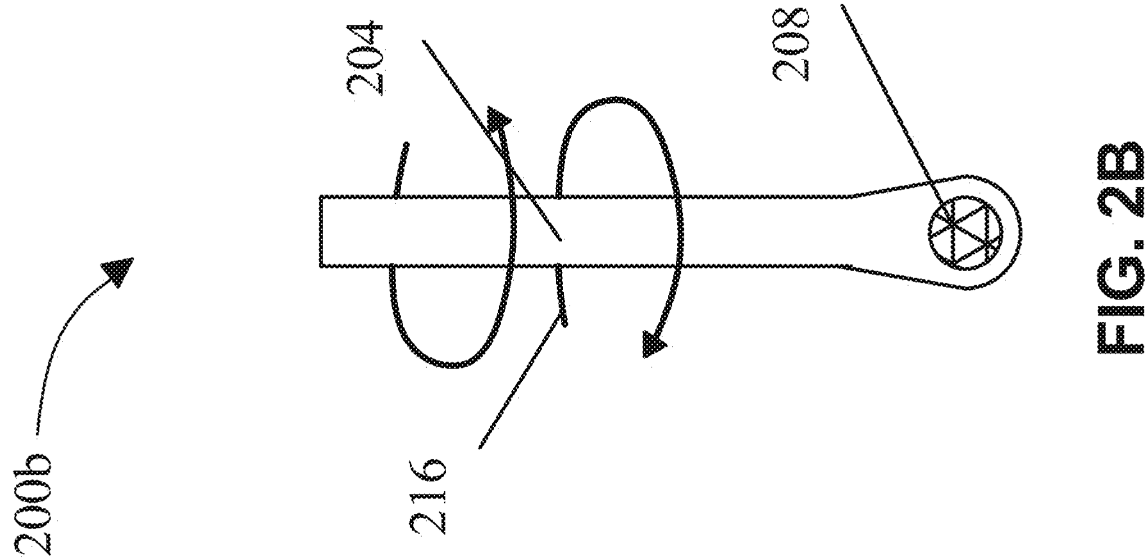
FIG. 2B is an exemplary illustration of a front view of at least a TEE probe with at least a transducer in a turning movement.

Referring now to FIG. 2B, an exemplary illustration 200*b* of a front view of at least a TEE probe with at least a transducer in a turning movement. In an embodiment, the illustration 200*b* may include at least a TEE probe 204. In an embodiment, the illustration 200*b* may include at least a transducer 208. In an embodiment, the illustration 200*b* may include a turning movement 216 of the at least a TEE probe 204. As used in this disclosure, a "turning movement" is the twisting motion of a TEE probe and/or its transducer around its longitudinal axis. In an embodiment, the turning movement 216 may be used to adjust the imaging angle and obtain different cross-sectional views of a structure. The turning movement 216 may allow for controlled rotation of the at least a transducer 208 to optimize visualization of anatomical features without advancing or withdrawing the TEE probe 204. Without limitation, the turning movement 216 may facilitate transitions between standard echocardiographic planes, such as rotating from a mid-esophageal four-chamber view to a mid-esophageal long-axis view, providing additional perspectives for diagnostic assessment and procedural guidance.

Figure 2C:
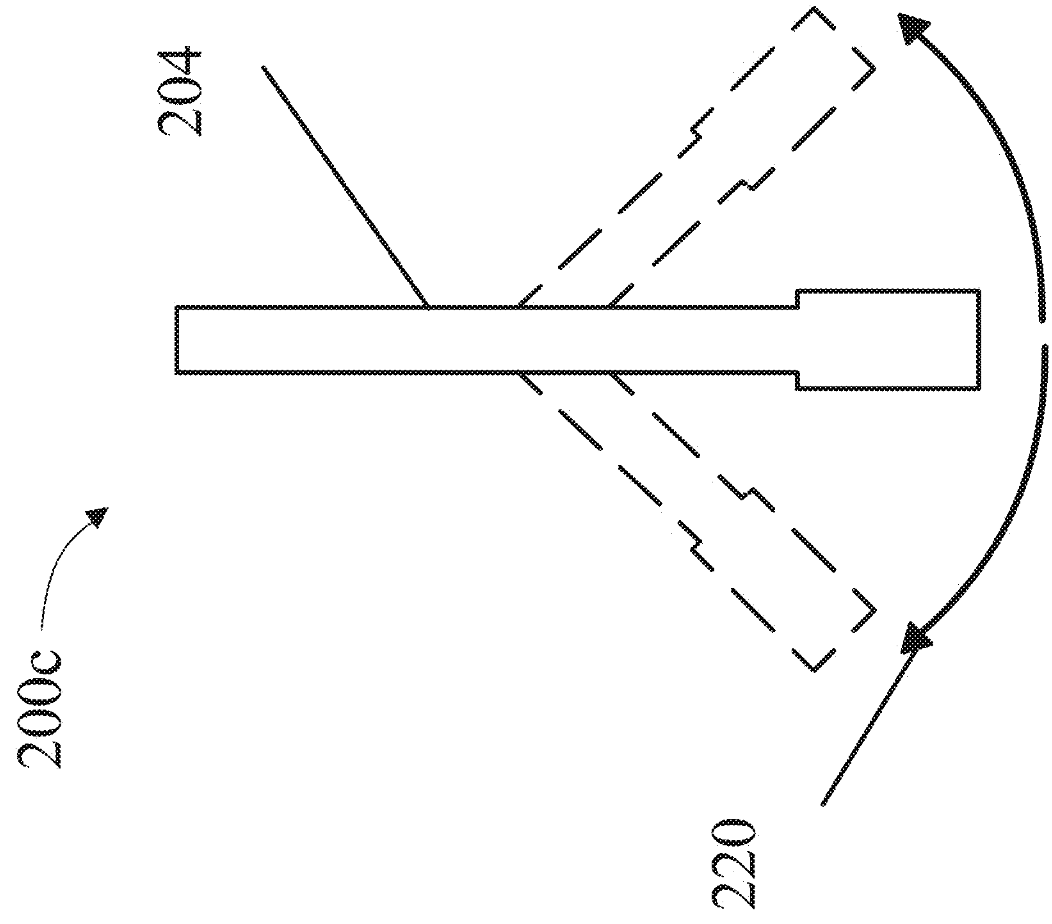
FIG. 2C is an exemplary illustration of a side view of at least a transducer in a retroflex and an anteflex movement.

Referring now to FIG. 2C, an exemplary illustration 200*c* of a side view of at least a transducer in a retroflex and an anteflex movement. In an embodiment, the illustration 200*c* may include at least a TEE probe 204. In an embodiment, the illustration 200*c* may include at least a transducer 208. In an embodiment, the illustration 200*c* may include a retroflex and an anteflex movement 220 of the at least a TEE probe 204. As used in this disclosure, a "retroflex movement" is the backward bending or angulation of a TEE probe tip. In an embodiment, the retroflex movement 220 may move the TEE probe 204 tip the toward the esophagus or stomach wall and may adjust the imaging angle and enhance visualization of posterior structures. Without limitation, the retroflex movement 220 may be used to obtain views such as the transgastric long-axis view, where the TEE probe 204 tip is flexed to better align with the left ventricular outflow tract and aortic valve. As used in this disclosure, an "anteflex movement" the forward bending or angulation of a TEE probe tip. In an embodiment, the anteflex movement 220 may include moving the TEE probe 204 tip toward the anterior aspect of the body to capture imaging of structures located more anteriorly in the chest. Without limitation, the anteflex movement 220 may assist in optimizing imaging of structures such as the mitral valve and left ventricular apex, particularly when performing detailed assessments of valvular function or guiding interventional procedures.

Figure 2D:
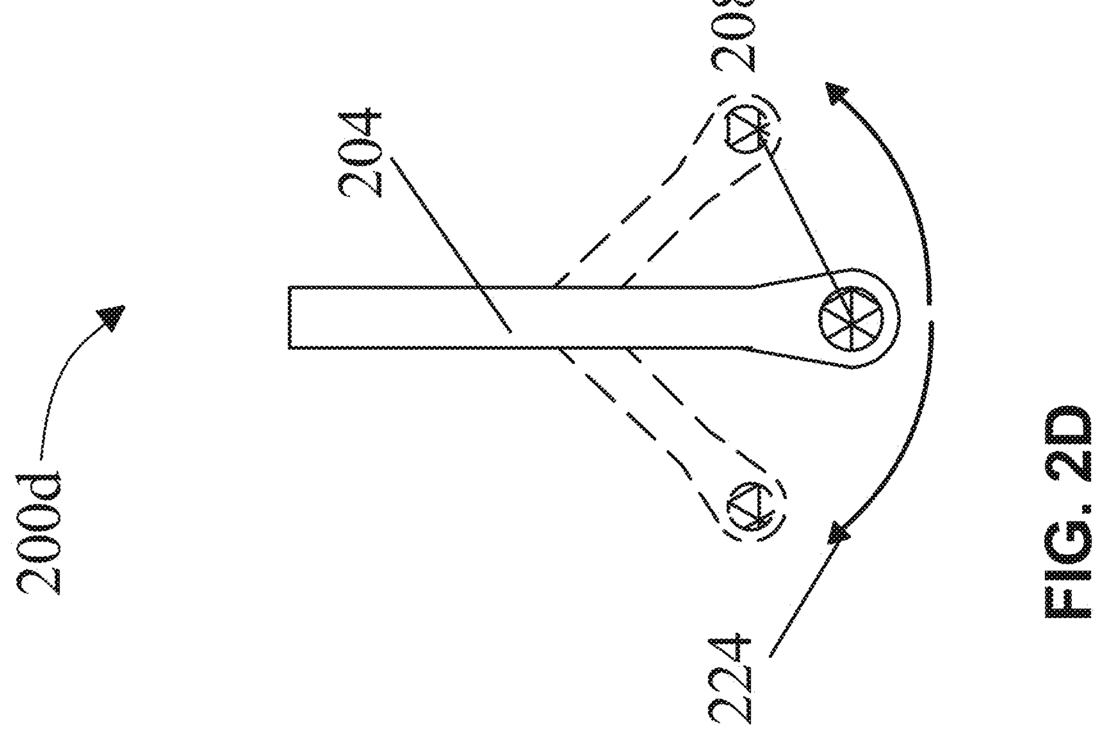
FIG. 2D is an exemplary illustration of a front view of at least a TEE probe with at least a transducer in a left flex and a right flex movement.
Figure 2E:
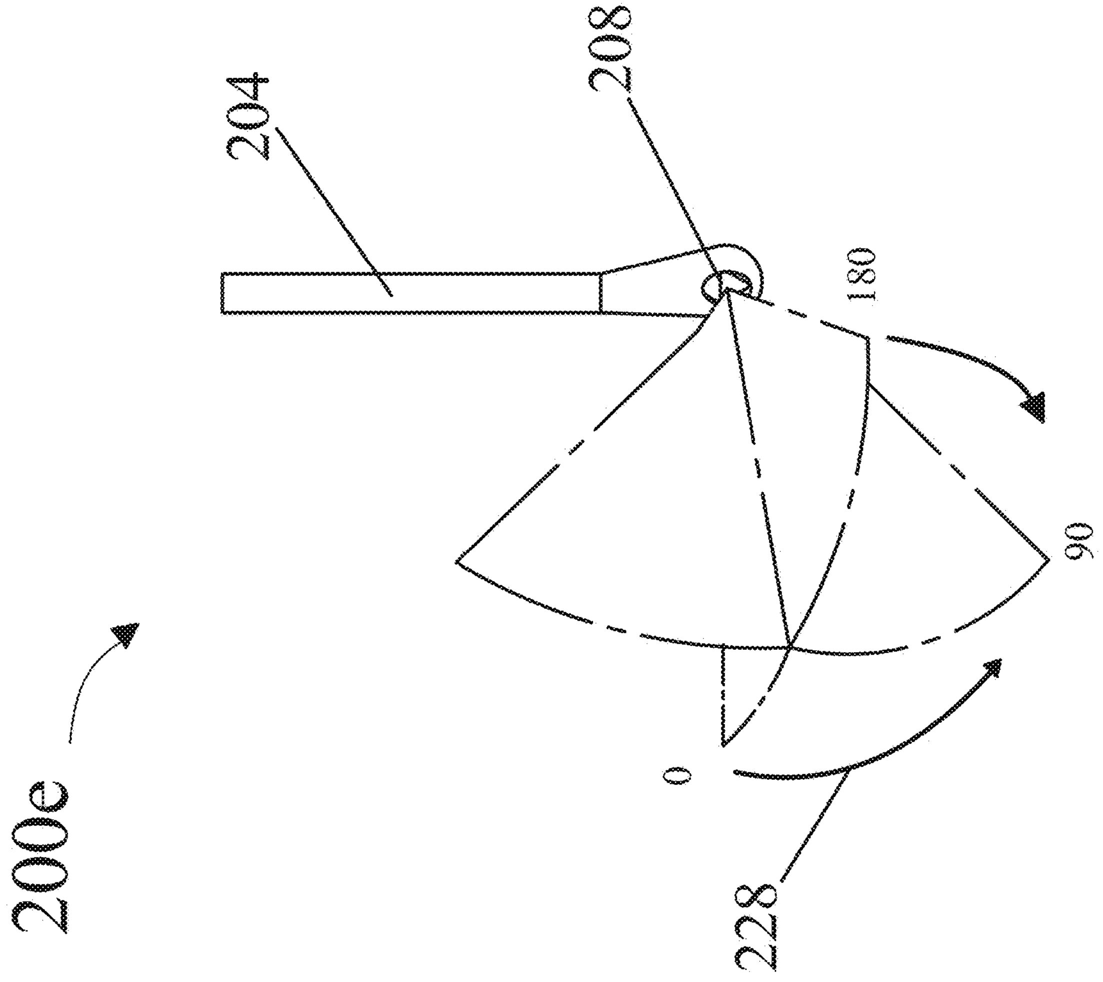
FIG. 2E is an exemplary illustration of an isometric view of at least a TEE probe with at least a transducer degrees of freedom.

Referring now to FIG. 2D, an exemplary illustration 200*d* of a front view of at least a TEE probe with at least a transducer in a left flex and a right flex movement. In an embodiment, the illustration 200*d* may include at least a TEE probe 204. In an embodiment, the illustration 200*d* may include at least a transducer 208. In an embodiment, the illustration 200*c* may include a left flex and a right flex movement 224 of the at least a TEE probe 204. As used in this disclosure, a "left flex movement" may refer to the lateral bending or angulation of a TEE probe tip. In an embodiment, the left flex movement 224 may move the TEE probe 204 tip toward the left side of the subject's body to adjust the imaging plane and optimize visualization of cardiac structures. The left flex movement 224 may be used to enhance imaging of the left atrium, left ventricle, and mitral valve, particularly when obtaining oblique or off-axis views for more comprehensive diagnostic assessments. As used in this disclosure, a "right flex movement" is the lateral bending or angulation of a TEE probe tip. In an embodiment, the right flex movement 224 may move the TEE probe 204 tip toward the right side of the subject's body to modify the imaging orientation and improve visualization of structures positioned more to the right. The right flex movement 224 may assist in capturing views of the right atrium, right ventricle, and tricuspid valve, enabling better assessment of right-sided heart function and potential abnormalities.

Referring now to FIG. 2E, an exemplary illustration 200*e* of an isometric view of at least a TEE probe with at least a transducer and degrees of freedom of movement. In an embodiment, the illustration 200*e* may include at least a TEE probe 204. In an embodiment, the illustration 200*e* may include at least a transducer 208. In an embodiment, the illustration 200*e* may include a rotating movement 228 of the at least a TEE probe 204. As used in this disclosure, "degrees of freedom of movement" is the independent directions in which a TEE probe or its transducer may be maneuvered. In an embodiment, the degrees of freedom of movement 228 may include advance movement (insertion), withdraw movement (retraction), retroflex movement (backward bending), anteflex movement (forward bending), left flex movement (lateral bending to the left), right flex movement (lateral bending to the right), and rotation movement (twisting around the longitudinal axis). Without limitation, these controlled movements may allow for precise positioning of the at least a transducer 208 to acquire optimal ultrasound images of anatomical structures, such as the heart, from multiple perspectives.

Figure 3:
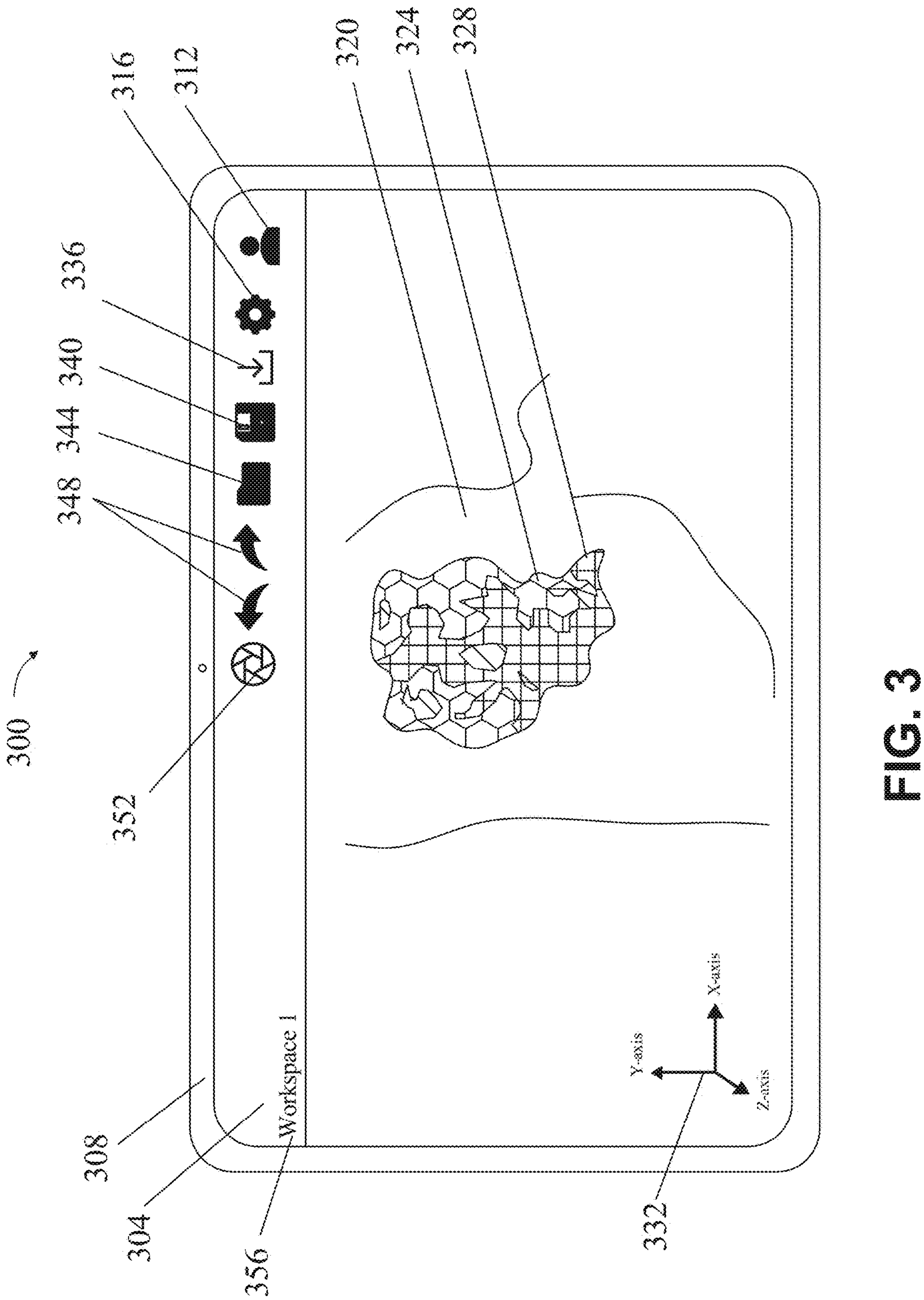
FIG. 3 is an exemplary illustration of a graphical user interface of a downstream device displaying a refined 3D model and a confidence score.

Referring now to FIG. 3, an exemplary illustration 300 of a graphical user interface of a downstream device displaying a refined 3D model and a confidence score. In an embodiment, the graphical user interface (GUI) 304 may be displayed on a downstream device 308. In an embodiment, the downstream device 308 may include a smartphone, tablet, or computer. In an embodiment, the GUI 304 may include a user profile icon 312. In an embodiment, the user profile icon 312 may serve as an interactive element that allows users to access and manage their personal account settings. In an embodiment, the user profile icon 312 may provide a direct link to the user's profile, where they may update personal information, review activity history, and configure preferences related to their interactions within the system. In an embodiment, the user profile icon 312 may enable users to modify details such as their name, contact information, medical history, or security settings. In an embodiment, the user profile icon 312 may serve as a gateway to account-related features, including login credentials, privacy controls, and system permissions. In an embodiment, the user profile icon 312 may support multi-user functionality, allowing different users to switch profiles or customize their experience within the same system. In an embodiment, the user profile icon 312 may incorporate a visual indicator, such as a profile picture placeholder, initials, or a silhouette, providing a recognizable representation of the user. In an embodiment, the user profile icon 312 may include a notification badge, alerting users to profile-related updates, messages, or required actions. In an embodiment, the user profile icon 312 may facilitate seamless user management and personalization within the GUI 304.

In an embodiment, the GUI 304 may include a gear icon 316. The GUI 304 may incorporate a gear icon 316, which may provide access to system settings, allowing users to customize preferences, adjust configurations, or manage administrative controls. In an embodiment, the GUI 304 may include at least a 3D model 320. In an embodiment, the at least a 3D model 320 may include at least a structure 324. In an embodiment, the at least a structure 324 may include a heart. In an embodiment, the at least a structure 324 may include color-coded confidence scoring 328. Without limitation, the color-coded confidence scoring 328 may provide a visual representation of the reliability of the at least a 3D model based on the confidence score. The color-coded confidence scoring 328 may indicate the accuracy and completeness of different regions within the reconstruction, allowing users to assess the trustworthiness of the displayed anatomical structures. Without limitation, the color-coded confidence scoring 328 may utilize a gradient or categorical color scheme, where higher-confidence areas may be displayed in green, representing well-defined structures reconstructed with high accuracy, while lower-confidence areas may appear in yellow or red, indicating potential uncertainties, missing data, or regions requiring further refinement. For example, without limitation, in an embodiment where the structure is a heart, the color-coded confidence scoring 328 may highlight the ventricular walls and valve leaflets in green if they were reconstructed from high-quality ultrasound data, while regions with motion artifacts or poor signal penetration, such as the left atrial appendage, may appear in yellow or red to signal lower confidence. The color-coded confidence scoring 328 may dynamically update as additional image data is incorporated, such as during subsequent sweeps of the TEE probe, allowing users to track improvements in model accuracy over time. The color-coded confidence scoring 328 may also be interactive, enabling users to hover over or select specific areas to view numerical confidence values or additional diagnostic insights. By incorporating the color-coded confidence scoring 328, the GUI 304 may enhance user interpretation, improve decision-making, and provide a clear, intuitive method for evaluating the reliability of the at least a 3D model during diagnostic assessments or interventional planning.

With continued reference to FIG. 3, in an embodiment, the GUI 304 may include a coordinate system 332. Without limitation, the coordinate system 332, which may provide a reference framework for positioning and/orienting the at least a 3D model within the display. The coordinate system 332 may allow users to visualize spatial relationships between structures and adjust viewing angles for improved interpretation. The coordinate system 332 may further assist in aligning image data from multiple sweeps, ensuring consistency in the reconstructed visualization. In an embodiment, the GUI 304 may include a download button 336. In an embodiment, the download button 336 may enable users to retrieve and store the displayed 3D model or related imaging data for offline analysis or external processing. The download button 336 may allow the export of files in various formats, such as DICOM, STL, or other compatible data structures, facilitating integration with different medical imaging systems or computational tools. In an embodiment, the GUI 304 may include a save button 340. Without limitation, the save button 340, which may allow users to store the current state of the at least a 3D model or any modifications made within the interactive visualization. The save button 340 may ensure that changes, annotations, or refined reconstructions are preserved for future review, enabling seamless continuity in clinical workflows or research applications. In an embodiment, the GUI 304 may include an open folder button 344. In an embodiment, the open folder button 344 may provide users with access to previously saved 3D models, image datasets, or reconstruction files. The open folder button 344 may facilitate efficient retrieval and management of stored imaging records, allowing for comparisons, longitudinal studies, or further refinement of earlier reconstructions. In an embodiment, the GUI 304 may include a undo/redo button 348. In an embodiment, the undo/redo button 348 may allow users to revert or reapply modifications made within the interactive visualization. The undo/redo button 348 may provide flexibility in adjusting the at least a 3D model, enabling users to explore different segmentation options, reconstructions, or annotation placements without losing previous adjustments.

With continued reference to FIG. 3, in an embodiment, the GUI 304 may include a capture button 352. Without limitation, the capture button 352 may enable users to perform a sweep using the at least a transducer and capture a sequence of ultrasound frames for reconstruction into the at least a 3D model. The capture button 352 may allow users to initiate and control the imaging process, ensuring that a complete dataset is acquired for volumetric reconstruction. The capture button 352 may also enable the recording of dynamic sweeps, providing continuous imaging across multiple planes to enhance the accuracy and completeness of the reconstruction. In some embodiments, the capture button 352 may allow users to adjust parameters such as sweep speed, depth range, or probe angulation, optimizing the acquisition process based on specific anatomical targets. For example, without limitation, in an embodiment where the structure is a heart, activating the capture button 352 may initiate a controlled sweep through mid-esophageal and transgastric views, ensuring comprehensive imaging of the left ventricle, right ventricle, and valve structures. The captured sweep data may then be processed by the 3D reconstruction model to generate a refined visualization for diagnostic assessment or procedural planning. The capture button 352 may further support real-time feedback, allowing users to review the acquired frames and determine if additional sweeps are needed to improve coverage or confidence in the model. Without limitation, by incorporating the capture button 352, the GUI 304 may facilitate efficient and precise imaging workflows, enhancing the quality of the at least a 3D model for clinical applications.

With continued reference to FIG. 3, in an embodiment, the GUI 304 may include a header 356. In an embodiment, the header 356 may display key information related to the at least a 3D model, including metadata such as patient details, scan date, imaging modality, or system status. The header 356 may provide a structured overview of essential data, improving usability and ensuring contextual awareness while navigating the visualization.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

Figure 4:
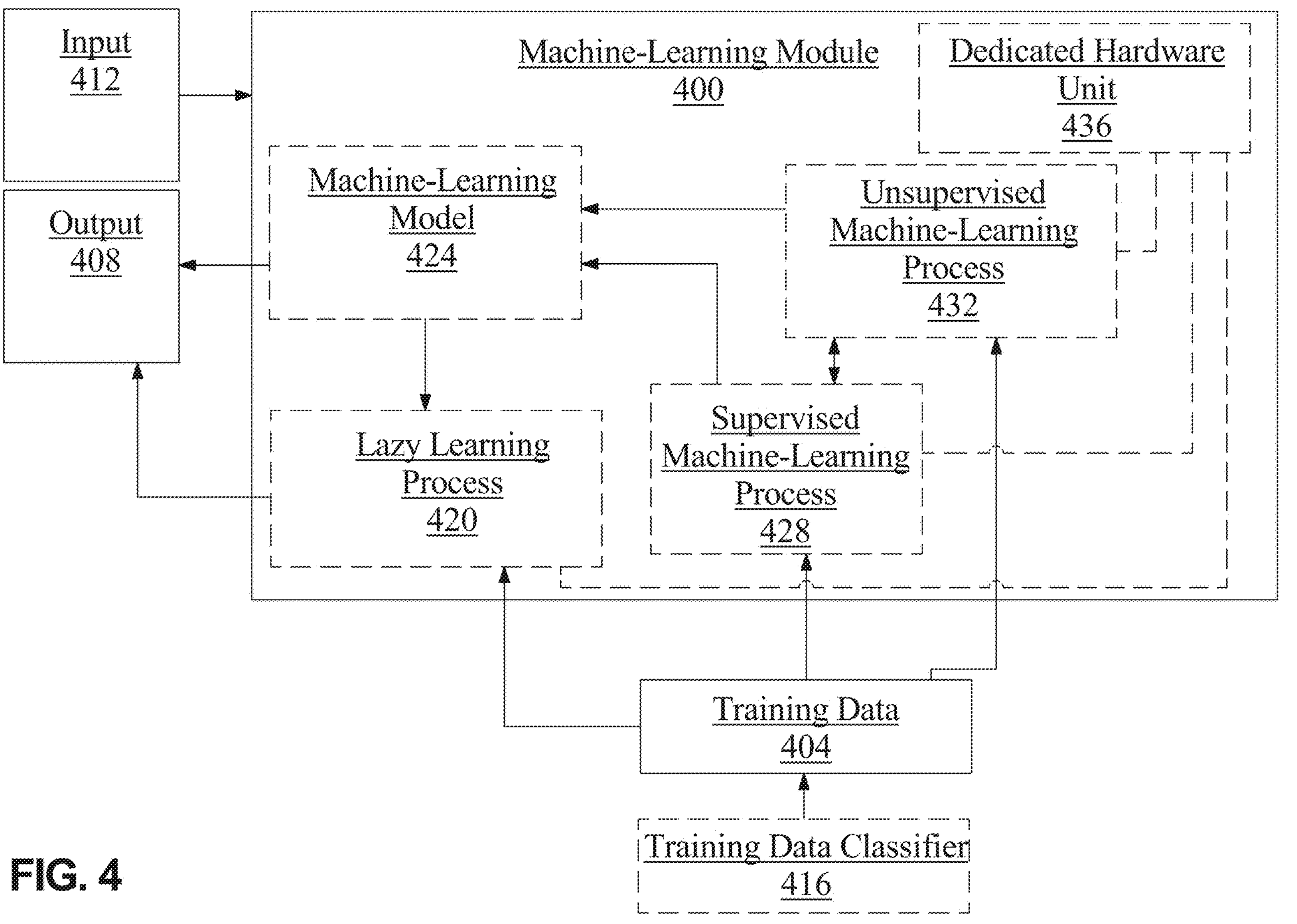
FIG. 4 is a block diagram of an exemplary machine-learning process.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example inputs such as image data and output at least a 3D model.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of image data based on characteristics that define a sub-population, such as a cohort of subjects, specific anatomical features, imaging conditions, or other analyzed parameters for which a subset of image data may be selected. The classification performed by training data classifier 416 may assist in optimizing the 3D reconstruction model by grouping relevant image data that shares similar attributes, ensuring improved accuracy and consistency in generating at least a 3D model.

Still referring to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include image data as described above as inputs, at least a 3D model as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods.

Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
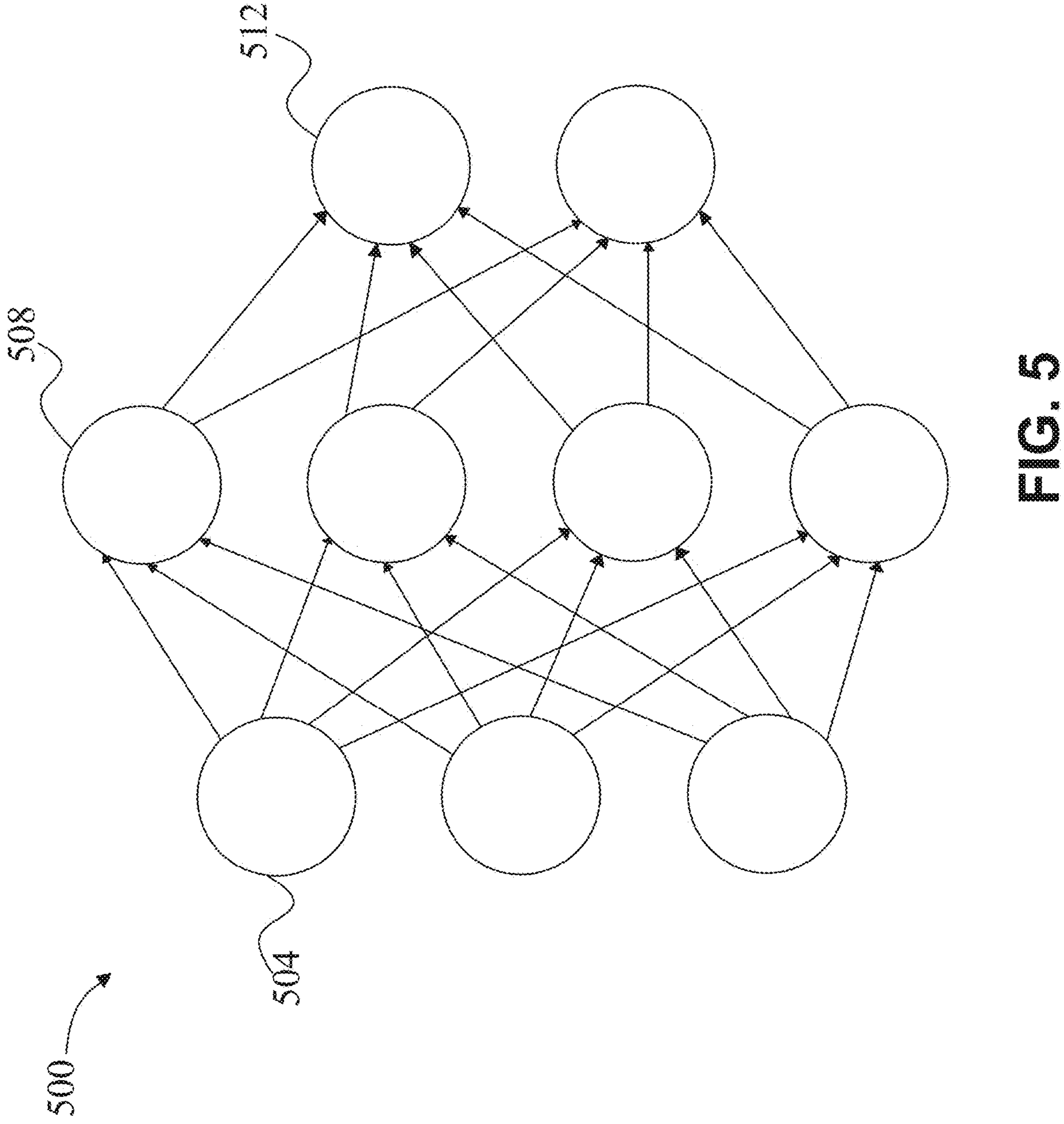
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
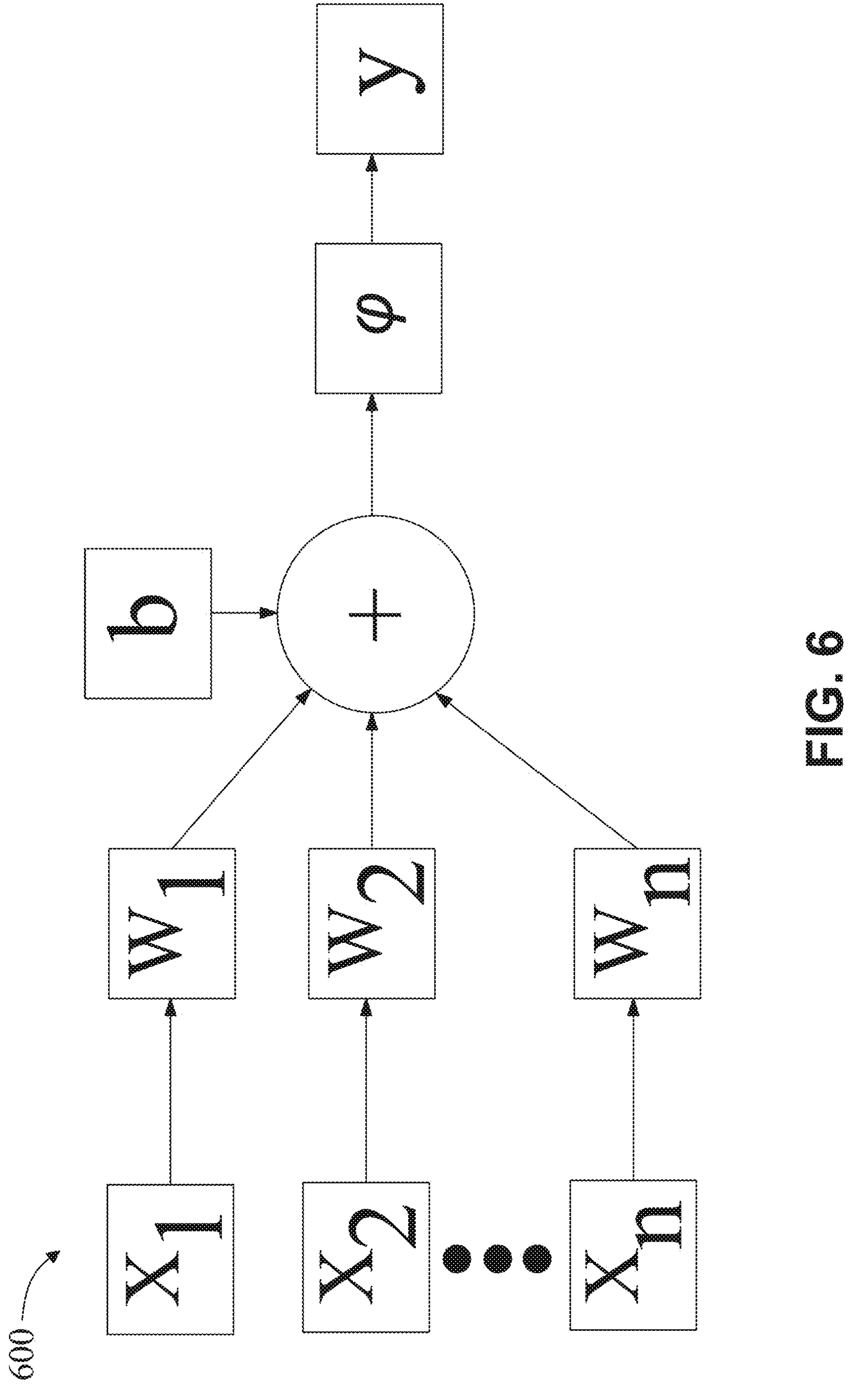
FIG. 6 is a diagram of an exemplary embodiment of a node of a neural network.

Referring now to FIG. 6, an exemplary embodiment of a node 600 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as f(x)=x*sigmoid(x), a Gaussian error linear unit function such as $$f(x) = a\left(1 + \tanh\left(\sqrt{2/\pi}\,(x + bx^r)\right)\right)$$

for some values of a, b, and r, and/or a scaled exponential linear unit function such as $$f(x) = \lambda\begin{cases} \alpha(e^x - 1) \text{ for } x < 0 \\ x \text{ for } x \leq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
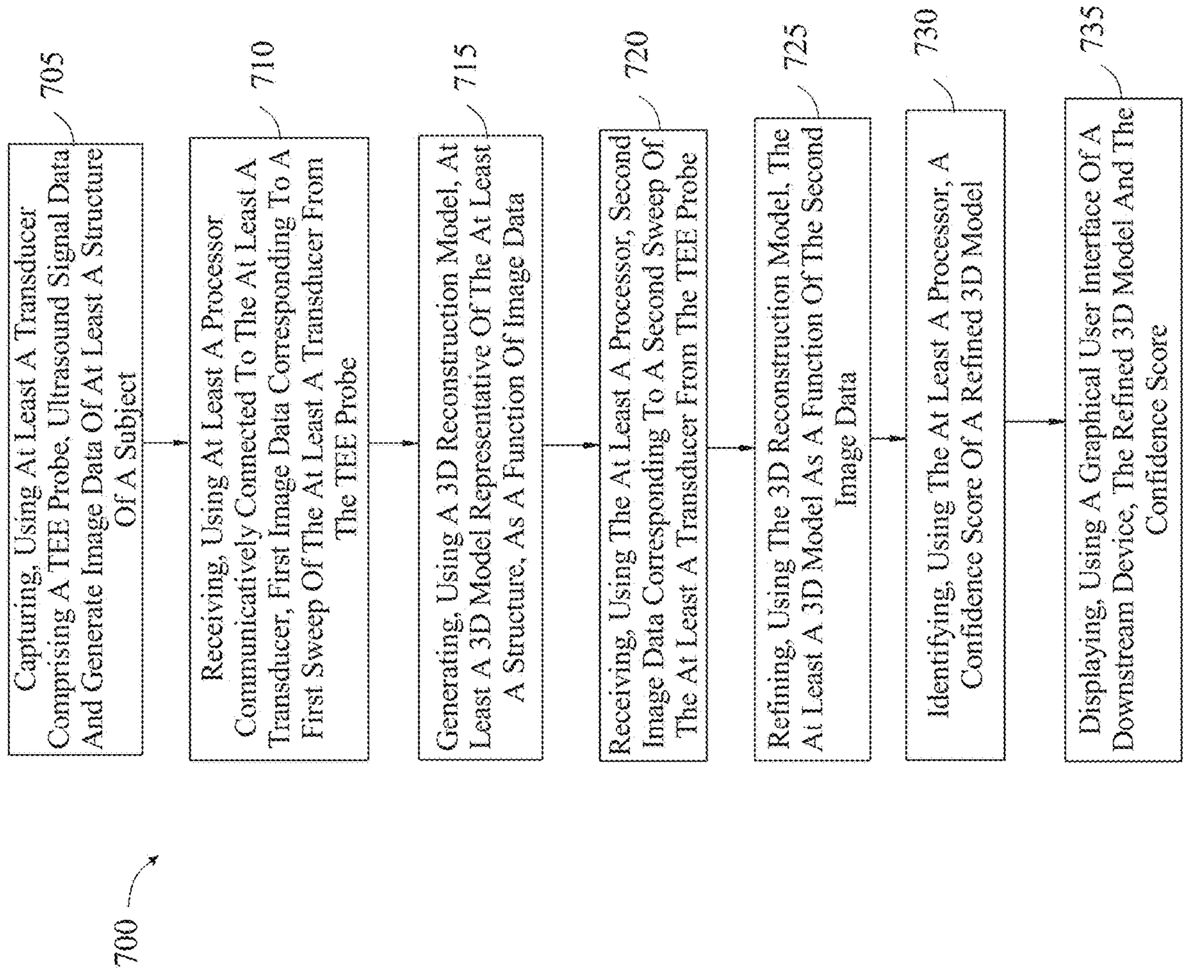
FIG. 7 is a block diagram of an exemplary method for reconstruction of anatomical structure using Transesophageal Echocardiography (TEE) imaging.

Referring now to FIG. 7, a flow diagram of an exemplary method 700 for reconstruction of anatomical structure using Transesophageal Echocardiography (TEE) imaging is illustrated. At step 705, method 700 includes capturing, using at least a transducer comprising a TEE probe, ultrasound signal data and generate image data of at least a structure of a subject. In an embodiment the at least a structure may include a heart. In an embodiment receiving the image data of the at least a transducer may include obtaining a sequence of ultrasound frames corresponding to multiple imaging planes of the at least a structure. This may be implemented as described and with reference to FIGS. 1-6.

Still referring to FIG. 7, at step 710, method 700 includes receiving, using at least a processor communicatively connected to the at least a transducer, first image data corresponding to a first sweep of the at least a transducer from the TEE probe. This may be implemented as described and with reference to FIGS. 1-6.

Still referring to FIG. 7, at step 715, method 700 includes generating, using a 3D reconstruction model, at least a 3D model representative of the at least a structure, as a function of image data. In an embodiment the at least a 3D model may include a scalar 3D field. In an embodiment the at least a 3D model may include a point cloud. In an embodiment generating the at least a 3D model representative of the at least a structure may include processing the image data using a machine-learning-based reconstruction algorithm to reconstruct volumetric representations of the at least a structure. In an embodiment the 3D reconstruction model may include a statistical shape model. This may be implemented as described and with reference to FIGS. 1-6.

Still referring to FIG. 7, at step 720, method 700 includes receiving, using the at least a processor, second image data corresponding to a second sweep of the at least a transducer from the TEE probe. This may be implemented as described and with reference to FIGS. 1-6.

Still referring to FIG. 7, at step 725, method 700 includes refining, using the 3D reconstruction model, the at least a 3D model as a function of the second image data. This may be implemented as described and with reference to FIGS. 1-6.

Still referring to FIG. 7, at step 730, method 700 includes identifying, using the at least a processor, a confidence score of a refined 3D model. In an embodiment the 3D reconstruction model may be configured to segment, using a segmentation algorithm, the at least a structure in each frame of the image data, determine, using the 3D reconstruction model, an orientation of the at least a transducer based on probe position data obtained from the transducer comprising the TEE probe, construct, using the 3D reconstruction model, a first 3D model of the at least a structure as a function of segmented image data and the orientation of the at least a transducer, and iteratively refine, using the 3D reconstruction model, the first 3D model using successive video frames of the second image data to generate the refined 3D model. In an embodiment iteratively refining, using the 3D reconstruction model, is a function of the confidence score and a plurality of subsequent sweeps, wherein the plurality of subsequent sweeps may include a plurality of image data. This may be implemented as described and with reference to FIGS. 1-6

Still referring to FIG. 7, at step 735, method 700 includes displaying, using a graphical user interface of a downstream device, the refined 3D model and the confidence score. In an embodiment displaying the at least a 3D model and the confidence score may include rendering an interactive visualization of the at least a 3D model on a graphical user interface and overlaying an indication of model reliability based on the confidence score. This may be implemented as described and with reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
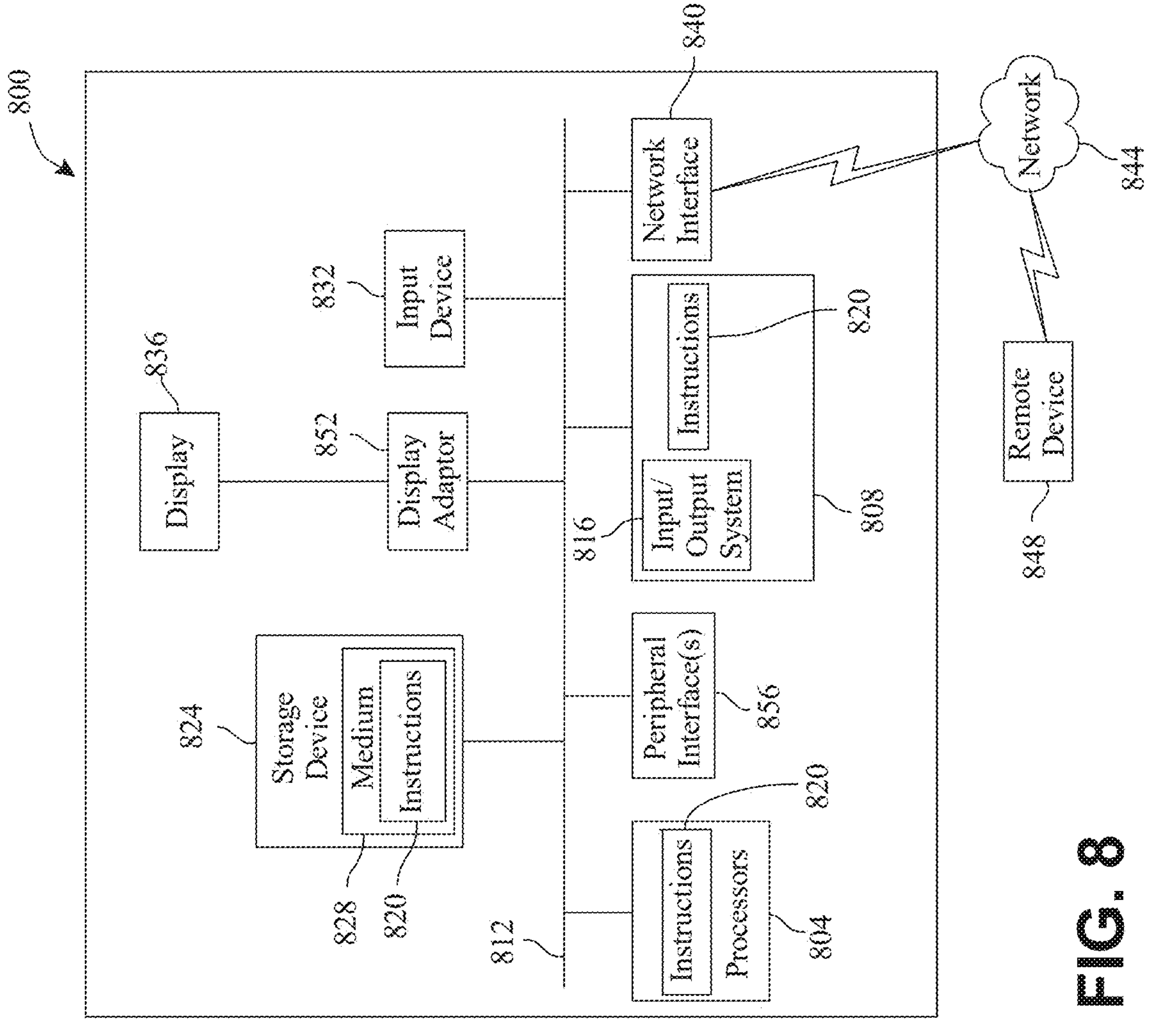
FIG. 8 is a block diagram of a computing system that can be used to implement any one or more of the methodologies disclosed herein and any one or more portions thereof.

FIG. 8 shows a diagrammatic representation of one embodiment of computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display device 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for reconstruction of anatomical structure using Transesophageal Echocardiography (TEE) imaging, wherein the apparatus comprises:

at least a TEE probe comprising at least a transducer, wherein the at least a transducer is configured to capture ultrasound signal data and generate image data of at least a structure of a subject;

at least a computing device, wherein the computing device is communicatively connected to the at least a transducer, the computing device comprises:

a memory; and at least a processor communicatively connected to the memory, wherein the memory contains instructions configuring the at least a processor to:

receive first image data corresponding to a first sweep of the at least a transducer from the TEE probe;

generate, using a 3D reconstruction model, at least a 3D model representative of the at least a structure, as a function of the first image data, wherein generating the at least a 3D model comprises:

segmenting, using a segmentation algorithm, the at least a structure in each frame of the image data;

determining, using the 3D reconstruction model, an orientation of the at least a transducer based on probe position data obtained from the transducer comprising the TEE probe; and constructing, using the 3D reconstruction model, a first 3D model of the at least a structure as a function of segmented image data and the orientation of the at least a transducer;

receive second image data corresponding to a second sweep of the at least a transducer from the TEE probe;

refine, using the 3D reconstruction model, the at least a 3D model as a function of the second image data, wherein refining the at least a 3D model comprises:

identifying using the at least a processor, a confidence score of a refined 3D model; and iteratively refining, using the 3D reconstruction model, the first 3D model using successive video frames of the second image data to generate the refined 3D model; and display, using a graphical user interface of a downstream device, the refined 3D model and the confidence score.

2. The apparatus of claim 1, wherein the first sweep and the second sweep comprise:

maintaining a static position and orientation of the TEE probe; and adjusting an orientation of the at least a transducer to acquire imaging data.

3. The apparatus of claim 1, wherein the at least a 3D model comprises a scalar 3D field.

4. The apparatus of claim 1, wherein the at least a 3D model comprises a point cloud.

5. The apparatus of claim 1, wherein receiving the image data of the at least a transducer comprises obtaining a sequence of ultrasound frames corresponding to multiple imaging planes of the at least a structure.

6. The apparatus of claim 1, wherein generating the at least a 3D model representative of the at least a structure comprises processing the image data using a machine-learning-based reconstruction algorithm to reconstruct volumetric representations of the at least a structure.

7. The apparatus of claim 1, wherein iteratively refining, using the 3D reconstruction model, is a function of the confidence score and a plurality of subsequent sweeps, wherein the plurality of subsequent sweeps comprise a plurality of image data.

8. The apparatus of claim 1, wherein the 3D reconstruction model comprises a statistical shape model.

9. The apparatus of claim 1, wherein displaying the at least a 3D model and the confidence score comprises rendering an interactive visualization of the at least a 3D model on a graphical user interface and overlaying an indication of model reliability based on the confidence score.

10. A method for reconstruction of anatomical structure using Transesophageal Echocardiography (TEE) imaging, wherein the method comprises:

capturing, using at least a transducer of a TEE probe, ultrasound signal data and generate image data of at least a structure of a subject;

receiving, using at least a processor communicatively connected to the at least a transducer, first image data corresponding to a first sweep of the at least a transducer from the TEE probe;

generating, using a 3D reconstruction model, at least a 3D model representative of the at least a structure, as a function of image data, wherein the 3D reconstruction model is configured to:

segment, using a segmentation algorithm, the at least a structure in each frame of the image data;

determine, using the 3D reconstruction model, an orientation of the at least a transducer based on probe position data obtained from the transducer comprising the TEE probe; and construct, using the 3D reconstruction model, a first 3D model of the at least a structure as a function of segmented image data and the orientation of the at least a transducer;

receiving, using the at least a processor, second image data corresponding to a second sweep of the at least a transducer from the TEE probe;

refining, using the 3D reconstruction model, the at least a 3D model as a function of the second image data, wherein refining the at least a 3D model comprises:

identifying, using the at least a processor, a confidence score of a refined 3D model; and iteratively refining, using the 3D reconstruction model, the first 3D model using successive video frames of the second image data to generate the refined 3D model; and displaying, using a graphical user interface of a downstream device, the refined 3D model and the confidence score.

11. The method of claim 10, wherein the first sweep and the second sweep comprise:

maintaining a static position and orientation of the TEE probe; and adjusting an orientation of the at least a transducer to acquire imaging data from different angular planes.

12. The method of claim 10, wherein the at least a 3D model comprises a scalar 3D field.

13. The method of claim 10, wherein the at least a 3D model comprises a point cloud.

14. The method of claim 10, wherein receiving the image data of the at least a transducer comprises obtaining a sequence of ultrasound frames corresponding to multiple imaging planes of the at least a structure.

15. The method of claim 10, wherein generating the at least a 3D model representative of the at least a structure comprises processing the image data using a machine-learning-based reconstruction algorithm to reconstruct volumetric representations of the at least a structure.

16. The method of claim 10, wherein iteratively refining, using the 3D reconstruction model, is a function of the confidence score and a plurality of subsequent sweeps, wherein the plurality of subsequent sweeps comprise a plurality of image data.

17. The method of claim 10, wherein the 3D reconstruction model comprises a statistical shape model.

18. The method of claim 10, wherein displaying the at least a 3D model and the confidence score comprises rendering an interactive visualization of the at least a 3D model on a graphical user interface and overlaying an indication of model reliability based on the confidence score.

* * * * *